United States Patent
Narayan

(10) Patent No.: US 9,393,425 B2
(45) Date of Patent: Jul. 19, 2016

(54) METHODS AND SYSTEMS FOR DETECTING AND TREATING HEART INSTABILITY

(71) Applicant: The Regents of the University of California, Oakland, CA (US)

(72) Inventor: Sanjiv Narayan, La Jolla, CA (US)

(73) Assignees: THE REGENTS OF THE UNIVERSITY OF CALIFORNIA, Oakland, CA (US); THE UNITED STATES OF AMERICA AS REPRESENTED BY THE DEPARTMENT OF VETERANS AFFAIRS, OFFICE OF THE GENERAL COUNSEL, Washington, DC (US)

(*) Notice: Subject to any disclaimer, the term of this patent is extended or adjusted under 35 U.S.C. 154(b) by 0 days.

(21) Appl. No.: 14/135,472

(22) Filed: Dec. 19, 2013

(65) Prior Publication Data
US 2014/0194763 A1 Jul. 10, 2014

Related U.S. Application Data

(63) Continuation of application No. 12/454,181, filed on May 12, 2009, now Pat. No. 8,676,303.

(60) Provisional application No. 61/052,970, filed on May 13, 2008.

(51) Int. Cl.
*A61B 5/04* (2006.01)
*A61N 1/365* (2006.01)
(Continued)

(52) U.S. Cl.
CPC .......... *A61N 1/36592* (2013.01); *A61B 5/0402* (2013.01); *A61B 5/0452* (2013.01);
(Continued)

(58) Field of Classification Search
CPC ................... A61B 18/1492; A61B 5/0422
See application file for complete search history.

(56) References Cited

U.S. PATENT DOCUMENTS

5,092,341 A * 3/1992 Kelen ............... A61B 5/0464
                                                                600/515
5,121,750 A     6/1992 Katims
(Continued)

FOREIGN PATENT DOCUMENTS

EP       0284685 A2    10/1988
WO    00/45700 A1     8/2000

OTHER PUBLICATIONS

Houben, R.P.M., et al, "Automatic mapping of human atrial fibrillation by template matching", Heart Rhythm, vol. 3, No. 10, Oct. 1, 2006, pp. 1221-1228.
(Continued)

*Primary Examiner* — Theodore Stigell
*Assistant Examiner* — Natasha Patel
(74) *Attorney, Agent, or Firm* — Eleanor Musick; Musick Davison, LLP

(57) ABSTRACT

Systems and methods define an index of risk for cardiac disease by detecting cellular derangements that may lead to cardiomyopathy, heart rhythm disorders or ischemic heart disease. The markers include fluctuations or abnormal rate-behavior of electrical, mechanical or other measurable biosignals. The invention operates in modes that can be applied to prevent atrial fibrillation or the risk for ventricular arrhythmias. Alternative embodiments are applied to tissue outside the heart such as skeletal muscle, smooth muscle, the central nervous system, the respiratory system, the urogenital system and the gastrointestinal system.

21 Claims, 21 Drawing Sheets

(51) Int. Cl.
*A61B 5/0402* (2006.01)
*A61B 5/00* (2006.01)
*A61N 1/362* (2006.01)
*A61B 5/0452* (2006.01)
A61B 5/0245 (2006.01)
A61B 18/14 (2006.01)
A61N 1/36 (2006.01)

(52) U.S. Cl.
CPC ............. *A61B5/4839* (2013.01); *A61B 5/7275* (2013.01); *A61B 18/14* (2013.01); *A61N 1/3621* (2013.01); *A61B 5/0245* (2013.01); *A61B 18/1492* (2013.01); *A61N 1/36114* (2013.01)

(56) References Cited

U.S. PATENT DOCUMENTS

| | | |
|---|---|---|
| 5,172,699 A | 12/1992 | Svenson et al. |
| 5,427,112 A | 6/1995 | Noren |
| 5,433,198 A | 7/1995 | Desai |
| 5,450,846 A | 9/1995 | Goldreyer |
| 5,458,621 A | 10/1995 | White |
| 5,480,422 A | 1/1996 | Ben-Haim |
| 5,487,391 A | 1/1996 | Panescu |
| 5,582,173 A | 12/1996 | Li |
| 5,645,070 A | 7/1997 | Turcott |
| 5,657,755 A | 8/1997 | Desai |
| 5,662,108 A | 9/1997 | Budd et al. |
| 5,687,737 A | 11/1997 | Branham et al. |
| 5,718,241 A | 2/1998 | Ben-Haim et al. |
| 5,795,303 A | 8/1998 | Swanson et al. |
| 5,810,740 A | 9/1998 | Paisner |
| 5,817,134 A | 10/1998 | Greenhut et al. |
| 5,840,025 A | 11/1998 | Ben-Haim |
| 5,848,972 A | 12/1998 | Triedman et al. |
| 5,868,680 A | 2/1999 | Steiner et al. |
| 5,954,665 A | 9/1999 | Ben-Haim |
| 6,052,618 A | 4/2000 | Dahlke et al. |
| 6,066,094 A | 5/2000 | Ben-Haim |
| 6,115,628 A | 9/2000 | Stadler et al. |
| 6,188,924 B1 | 2/2001 | Swanson et al. |
| 6,208,888 B1 | 3/2001 | Yonce |
| 6,236,883 B1 | 5/2001 | Ciaccio et al. |
| 6,256,540 B1 | 7/2001 | Panescu et al. |
| 6,301,496 B1 | 10/2001 | Reisfeld |
| 6,360,121 B1 | 3/2002 | Shoda |
| 6,438,406 B2 | 8/2002 | Yonce |
| 6,438,409 B1 | 8/2002 | Malik et al. |
| 6,449,503 B1 | 9/2002 | Hsu |
| 6,522,905 B2 | 2/2003 | Desai |
| 6,584,345 B2 | 6/2003 | Govari |
| 6,847,839 B2 | 1/2005 | Ciaccio et al. |
| 6,856,830 B2 | 2/2005 | He |
| 6,892,091 B1 | 5/2005 | Ben-Haim et al. |
| 6,920,350 B2 | 7/2005 | Xue et al. |
| 6,941,166 B2 | 9/2005 | MacAdam et al. |
| 6,950,696 B2 | 9/2005 | Bjorling et al. |
| 6,959,212 B2 | 10/2005 | Hsu et al. |
| 6,975,900 B2 | 12/2005 | Rudy et al. |
| 6,978,168 B2 | 12/2005 | Beatty et al. |
| 7,016,719 B2 | 3/2006 | Rudy et al. |
| 7,043,292 B2 | 5/2006 | Tarjan et al. |
| 7,117,030 B2 | 10/2006 | Berenfeld et al. |
| 7,123,954 B2 | 10/2006 | Narayan et al. |
| 7,206,630 B1 | 4/2007 | Tarler |
| 7,245,962 B2 | 7/2007 | Ciaccio et al. |
| 7,263,397 B2 | 8/2007 | Hauck et al. |
| 7,283,865 B2 | 10/2007 | Noren |
| 7,289,843 B2 | 10/2007 | Beatty et al. |
| 7,328,063 B2 | 2/2008 | Zhang et al. |
| 7,505,810 B2 | 3/2009 | Harlev et al. |
| 7,515,954 B2 | 4/2009 | Harlev et al. |
| 7,734,333 B2 | 6/2010 | Ghanem et al. |
| 7,751,882 B1 | 7/2010 | Helland |
| 7,761,142 B2 | 7/2010 | Ghanem et al. |
| 7,761,150 B2 | 7/2010 | Ghanem et al. |
| 7,907,994 B2 | 3/2011 | Stolarski et al. |
| 7,930,018 B2 | 4/2011 | Harlev et al. |
| 7,930,020 B2 | 4/2011 | Zhang et al. |
| 7,953,475 B2 | 5/2011 | Harlev et al. |
| 7,962,202 B2 | 6/2011 | Bhunia |
| 8,050,732 B2 | 11/2011 | Desai |
| 8,050,751 B2 | 11/2011 | Zhang et al. |
| 8,095,205 B2 | 1/2012 | Bhunia |
| 8,095,206 B2 | 1/2012 | Ghanem et al. |
| 8,165,666 B1 | 4/2012 | Briggs et al. |
| 8,165,671 B2 | 4/2012 | Freeman et al. |
| 8,175,702 B2 | 5/2012 | Efimov et al. |
| 8,340,766 B2 | 12/2012 | Ryu et al. |
| 8,386,024 B2 | 2/2013 | Gunderson et al. |
| 8,521,266 B2 | 8/2013 | Narayan et al. |
| 8,594,777 B2 | 11/2013 | Briggs et al. |
| 8,639,325 B2 | 1/2014 | Efimov et al. |
| 8,676,303 B2 | 3/2014 | Narayan |
| 8,700,140 B2 | 4/2014 | Narayan et al. |
| 8,838,222 B2 | 9/2014 | Narayan et al. |
| 8,838,223 B2 | 9/2014 | Narayan et al. |
| 2002/0010392 A1 | 1/2002 | Desai |
| 2003/0018277 A1 | 1/2003 | He |
| 2003/0083587 A1 | 5/2003 | Ferek-Petric |
| 2003/0236466 A1 | 12/2003 | Tarjan |
| 2004/0059237 A1* | 3/2004 | Narayan et al. ............... 600/509 |
| 2004/0073262 A1 | 4/2004 | Lovett |
| 2005/0027321 A1* | 2/2005 | Ferek-Petric ..................... 607/9 |
| 2005/0148892 A1 | 7/2005 | Desai |
| 2005/0203502 A1 | 9/2005 | Boveja et al. |
| 2006/0084970 A1 | 4/2006 | Beatty et al. |
| 2006/0161206 A1 | 7/2006 | Efimov et al. |
| 2007/0055167 A1 | 3/2007 | Bullinga |
| 2007/0208260 A1 | 9/2007 | Afonso |
| 2007/0232948 A1 | 10/2007 | Stadler et al. |
| 2007/0299351 A1 | 12/2007 | Harlev et al. |
| 2008/0097539 A1 | 4/2008 | Belalcazar |
| 2008/0109041 A1 | 5/2008 | De Voir |
| 2008/0114258 A1 | 5/2008 | Zhang et al. |
| 2008/0188765 A1 | 8/2008 | Stolarski et al. |
| 2009/0069704 A1 | 3/2009 | MacAdam et al. |
| 2009/0099468 A1 | 4/2009 | Thiagalingam et al. |
| 2009/0112106 A1 | 4/2009 | Zhang et al. |
| 2009/0112110 A1 | 4/2009 | Zhang et al. |
| 2009/0112199 A1 | 4/2009 | Zhang et al. |
| 2009/0177071 A1 | 7/2009 | Harlev et al. |
| 2009/0177072 A1 | 7/2009 | Harlev et al. |
| 2009/0299424 A1 | 12/2009 | Narayan |
| 2010/0094274 A1 | 4/2010 | Narayan |
| 2010/0204592 A1 | 8/2010 | Hatib et al. |
| 2010/0217143 A1 | 8/2010 | Whittington et al. |
| 2010/0249627 A1 | 9/2010 | Zhang |
| 2010/0298729 A1 | 11/2010 | Zhang et al. |
| 2010/0305456 A1 | 12/2010 | Brainard, II |
| 2011/0087121 A1 | 4/2011 | Zhang et al. |
| 2011/0112425 A1 | 5/2011 | Muhlsteff et al. |
| 2011/0130801 A1 | 6/2011 | Maskara et al. |
| 2011/0196249 A1 | 8/2011 | Staeuber et al. |
| 2011/0251505 A1 | 10/2011 | Narayan |
| 2011/0257547 A1 | 10/2011 | Zhang et al. |
| 2011/0282227 A1 | 11/2011 | Zhang |
| 2012/0184858 A1 | 7/2012 | Harlev et al. |
| 2012/0232417 A1 | 9/2012 | Zhang et al. |
| 2013/0006131 A1 | 1/2013 | Narayan et al. |
| 2013/0150740 A1 | 6/2013 | Narayan et al. |
| 2013/0150742 A1 | 6/2013 | Briggs et al. |
| 2013/0226016 A1 | 8/2013 | Narayan et al. |
| 2013/0324871 A1 | 12/2013 | Dubois et al. |
| 2013/0331718 A1 | 12/2013 | Narayan et al. |
| 2013/0345577 A1 | 12/2013 | Thakur et al. |
| 2014/0005562 A1 | 1/2014 | Bunch et al. |
| 2014/0066787 A1 | 3/2014 | Narayan et al. |
| 2014/0073981 A1 | 3/2014 | Narayan et al. |

(56) References Cited

U.S. PATENT DOCUMENTS

| | | |
|---|---|---|
| 2014/0114204 A1 | 4/2014 | Narayan et al. |
| 2014/0228696 A1 | 8/2014 | Narayan et al. |
| 2014/0276152 A1 | 9/2014 | Narayan et al. |

OTHER PUBLICATIONS

Nademanee, Koonlawee, et al., "A new approach for catheter ablation of atrial fibrillation: mapping of the electrophysiologic substrate", J. Amer.Coll.Cardiol., vol. 43, No. 11, Jun. 2, 2004, pp. 2044-2053.

Narayan, S.M., et al., "Dynamics factors preceding the initiation of atrial fibrillation in humans", Heart Rhythm, vol. 5, No. 6, Jun. 1, 2008, pp. S22-S25.

Ciaccio, Edward J. et al., "Development of Gradient Descent Adaptive Algorithms to Remove Common Mode Artifact for Improvement of Cardiovascular Signal Quality", Annals of Biomedical Engineering, vol. 35, No. 7, Jul. 2007, pp. 1146-1155.

Sornborger, Andrew, et al., "Extraction of Periodic Multivariate Signals: Mapping of Voltage-Dependent Dye Fluorescence in the Mouse Heart", IEEE Transactions on Medical Imaging, vol. 22, No. 12, Dec. 2003, pp. 1537-1549.

Sun, Yan, et al., "Characteristic wave detection in ECG signal using morphological transform", BMC Cardiovascular Disorders, vol. 5, No. 28, 2005.

Tai, Dean C.S., et al., "Correction of motion artifact in transmembrane voltage-sensitive fluorescent dye emission in hearts", Am. J. Physiol. Heart Circ. Physiol., vol. 287, 2004, pp. H985-H993.

Lin, Y-J, et al., "Electrophyiological Characteristics and Catheter Ablation in Patients With Paroxysmal Right Atrial Fibrillation", Circulation, Sep. 20, 2005; 112(12): 1692-1700, EPub Sep. 12, 2005.

Houben, R.P.M., et al., "Processing of Intracardiac Electrograms in Atrial Fibrillation", IEEE Engineering in Medicine and Biology Magazine, Nov./Dec. 2006, pp. 40-51.

Saksena, S., et al., "Regional Endocardial Mapping of Spontaneous and Induced Atrial Fibrillation in Patients With Heart Disease and Refractory Atrial Fibrillation", Am J Cardiol, 1999; 84:880-889.

EP 12711553 Supplementary European Search Report & European Search Opinion, Sep. 11, 2013, 7 pages.

PCT/US2012/029935 International Search Report and Written Opinion, Nov. 8, 2012, 9 pages.

EP 09819953 Supplementary European Search Report & European Search Opinion Feb. 7, 2012, 12 pages.

PCT/US2011/031468 International Preliminary Report on Patentability and Written Opinion, Oct. 9, 2012, 8 pages.

PCT/US2011/031470 International Preliminary Report on Patentability and Written Opinion, Oct. 9, 2012, 7 pages.

PCT/US2009/060178 International Preliminary Report on Patentability and Written Opinion, Apr. 12, 2011, 10 pages.

PCT/US2012/036157 International Preliminary Report on Patentability and Written Opinion, Aug. 14, 2012, 8 pages.

PCT/US2012/068639 International Preliminary Report on Patentability and Written Opinion, Jun. 10, 2013; 6 pages.

PCT/US/2014/029645 International Search Report and Written Opinion, Aug. 18, 2014, 17 pages.

PCT/US2012/068640 International Preliminary Report on Patentability and Written Opinion, Jun. 10, 2013; 5 pages.

PCT/US2014/029616 International Search Report and Written Opinion, Sep. 18, 2014; 9 pages.

Umapathy, K, et al. "Spatiotemporal Frequency Analysis of Ventricular Fibrillation in Explanted Human Hearts," IEEE Transactions on Biomedical Engineering, vol. 56, No. 2, Feb. 1, 2009, pp. 328-335.

Kalifa, J, et al. "Mechanisms of wave fractionation at boundaries of high-frequency excitation in the posterior left atrium of the isolated sheep heart during atrial fibrillation," Circulation, vol. 113, No. 5, Feb. 7, 2006, pp. 626-633.

Yenn-Jiang L, et al. "Electrophysiological Mechanisms and Catheter Ablation of Complex Atrial Arrhythmias from Crista Terminalis: Insight from Three-Dimentional Noncontact Mapping," Pacing and Clinical Electrophysiology, vol. 27, No. 9, Sep. 1, 2004, pp. 1231-1239.

Holm, M. et al., "A New Method for Analysis of Atrial Activation During Chronic Atrial Fibrillation in Man", IEEE Transactions on Biomedical Engineering, vol. 43, No. 2, Feb. 1, 1996, pp. 198-210.

Ulphani, J.S., et al., "Frequency gradients during two different forms of fibrillation in canine atria", Heart Rhythm, vol. 4, No. 10, Oct. 2007, pp. 1315-1323.

Kadish, A., et al., "Characterization of fibrillatory rhythms by ensemble vector directional analysis", Am J Physiol.—Heart Circ. Physiol., vol. 285, Oct. 2003, pp. H1705-H1719.

Masse, S., et al., "Wave similarity of human ventricular fibrillation from bipolar electrograms",Eurospace (2007) vol. 9, pp. 10-19.

EP12855266.8: Supplementary European Search Report & European Search Opinion, Jun. 2, 2015, 9 pages.

\* cited by examiner

METHODS AND SYSTEMS FOR DETECTING AND TREATING HEART INSTABILITY

GOVERNMENT RIGHTS

The present invention was made with government support under Grants HL070529 and HL083359 awarded by the National Institutes of Health. The Government has certain rights in the invention. sp

RELATED APPLICATIONS

This application is a continuation of application Ser. No. 12/454,181, filed May 12, 2009, now issued as U.S. Pat. No. 8,676,303, which claims the benefit of priority of Provisional Application No. 61/052,970, filed May 13, 2008, which is incorporated herein by reference in its entirety.

BACKGROUND

1. Field of the Invention

The invention relates generally to the field of medicine and more specifically to machines and processes for monitoring heart instability.

2. Background Art

Heart rhythm disorders are extremely common in the United States, and cause significant mortality and morbidity. However, there are few methods to predict future rhythm disorders ("arrhythmias") before they occur. Instead, physicians rely upon detecting the actual rhythm disturbance, which precludes early detection and possible prevention of these disorders. Many methods currently used also may have serious side-effects. Over 2 million Americans suffer from Atrial Fibrillation (AF), a rhythm disorder of the atria (top heart chambers) that causes serious symptoms, lost days from work, and potentially death (Chugh, Blackshear et al. 2001). Sadly, AF sometimes is first detected after it has caused a serious side-effect such as a stroke. Predicting the future development of AF in an individual can prevent such catastrophic events. However, clinical practice is so rudimentary in this area that it relies upon observing episodes of AF to detect future risk, yet many episodes of AF are still missed or misclassified (Chugh, Blackshear et al. 2001). Therefore, prediction of AF has been difficult.

The same problems exist for predicting a variety of important heart instabilities. Sudden cardiac arrest is the leading cause of mortality in the U.S., taking over 300,000 lives per year, largely due to the rhythm disorders of ventricular tachycardia (VT) or fibrillation (VF) (Myerburg and Castellanos 2006). Current methods of predicting future VT/VF are inadequate. In fact, risk is often not identified until after sudden cardiac arrest (SCA) occurs—despite the fact that an individual's chance for surviving out-of-hospital SCA is <10% (Robertson 2000). The inability to predict future VT/VF also leads to a potential overuse of preventive therapy in the form of the implantable cardioverter defibrillators (Myerburg and Castellanos 2006).

The field is replete with attempts to detect these disorders. For instance, it has been shown that human AF, VT and VF, as well as other less serious heart rhythm disorders, can arise by the mechanism of reentry (Kuo, Munakata et al. 1983). In this case, barriers (known as "conduction blocks") can develop and cause otherwise orderly electrical impulses to disorganize into electrical waves that circulate around the barrier. In addition, localized regions of scar tissue or ischemic tissue propagate electrical activity (depolarization) slower than normal tissue, causing "slow conduction," which may factor into formation of these wavelets. This may lead to errant, circular propagation. Further, "reentry" or "circus motion" may result, which disrupts depolarization and contraction of the atria or ventricles, and leads to abnormal rhythms ("arrhythmias"). Many tools have been developed to predict rhythm disorders from these large-scale effects, with suboptimal results.

AF often occurs in patients in whom the atria, the top chamber of the heart, is enlarged or weakened. However, whether the AF is the cause or effect of the atrial cardiomyopathy ("heart failure of the atrium") has been unclear.

In one study (Narayan, Bode et al. 2002b), it is shown that action potential oscillations during atrial flutter (a different abnormal heart rhythm) may enable the transition to AF. However, action potential oscillations during atrial flutter occur in only a small minority of sufferers with AF. In addition, the study observed only the right atrium. However, the left atrium is critical in the initiation of AF, and is the chamber in which treatment for AF is most effective (Calkins et al., 2007). Action potential fluctuations also arise in the left atrium near the pulmonary veins, which leads to AF in a large number of cases (Calkins et al, 2007).

Previous studies from patients with atrial cardiomyopathy undergoing surgery revealed tissue specimens that showed atrium enlargement, weakening of atrial wall contractions, thickening of atrial walls, and cell loss and destruction in cases of cardiomyopathy of the atrium (Frustaci, Chimenti et al. 1997). Often, but not always, these signs are secondary to disease of the ventricles. However, testing using tissue specimens is not a viable clinical tool. Taking tissue from the heart (biopsy) is a risky procedure that may potentially cause serious side-effects including death. In the atrium, this is almost never performed unless a patient is proceeding to surgery for another reason.

Echocardiography can show weakening of contraction and enlargement of the atrium. However, this does not specifically indicate any disease. In fact, weakening can be seen in individuals without primary atrial cardiomyopathy or AF, who may have other common and even non-serious diseases of the ventricles including left ventricular hypertrophy from mild high blood pressure (Thomas, Levett et al. 2002). Weakening and fibrosis of the wall of the atrium can slow electrical conduction through its walls. This leads to a prolonged P-wave duration on the surface ECG. Many studies have used this measurement to predict AF (Steinberg, Prystowski et al. 1994), but with modest results because this factor may not be central to all forms of AF (AF can arise in individuals without atrial fibrosis or conduction slowing). As a result, these and related measurements are not often used clinically.

Other methods used to assess atrial function include elevated levels of natriuretic peptides, yet these methods have not been incorporated into clinical practice in humans because their predictive value is also poor (Therkelsen, Groenning et al. 2004). Other methods exist to measure atrial size, including magnetic resonance imaging and other techniques, yet these methods do not correlate with atrial function. As a result, these methods are not used in clinical practice.

Methods that have been proposed to predict AF risk, or track propensity, are non-specific and not often used. Common methods include clinical associations, such as identifying-individuals with thyroxicosis or heart valve disease as having increased risk for AF. Further, individuals with ventricular disease have higher left atrial pressures which may predispose them to developing AF. Such ventricular diseases include simple ones (left ventricular hypertrophy from aging or high blood pressure), and more complex ones (ventricular cardiomyopathy). Other methods include identifying a large left atrial size on imaging (echocardiography, MRI). However, none of these clinical associations accurately identifies which individuals will develop AF, or when.

Other methods have been described that focus on reentrant mechanisms for AF, but are also not used clinically. Steinberg et al. (Steinberg, Zelenkofske et al. 1993a), Klein et al. (Klein, Evans et al. 1995) and others showed that prolonged atrial activity indicates slow conduction which identifies patients at risk for AF. Work by Narayan et al. (Narayan, Bode et al. 2002b) suggested that the presence of alternate beat variations ("alternans") of the timing, shape or amplitude of the P-wave (or an atrial signal surrogate) predicts AF. However, those studies pertained only to patients with existing atrial flutter (a related rhythm disorder) in the right atrium (that is less important for AF), and used pacing for studying some of the patients. Thus, the studies did not demonstrate results relevant to most patients with AF, who do not have preceding atrial flutter. Other methods include detecting abnormalities of the sinus node rate that may precede AF (Faddis, Narayan et al. 1999), but also have limited predictive value.

Methods directed to preventing heart rhythm disorders propose fast pacing rates for prevention of arrhythmias, such as overdrive pacing (at faster rates than observed naturally in the individual). These methods have had very limited success.

Atrial cardiomyopathy (heart failure of the top chamber of the heart) is a relatively new concept, and is not often diagnosed clinically. As a result, few therapies have been described to treat atrial cardiomyopathy. However, there is increasing interest in methods of improving atrial function.

New evidence suggests that drugs such as angiotensin-receptor antagonists and angiotensin receptor blockers can prevent atrial fibrosis and progression of atrial cardiomyopathy (Wachtell, Lehto et al. 2005). Similar benefits have been shown for beta-receptor antagonists, and also for agents such as HMG co-A reductase inhibitors (Ehrlich, Biliczki et al. 2008). However, these drugs act over years, not acutely, and it is unclear how well they reverse or stabilize atrial cardiomyopathy that has already developed. Further, many of these drug benefits were discovered indirectly in trials designed to examine benefits of the drugs on ventricular function. Thus, it is not clear if the drugs would lead to similar benefits in direct prospective trials, and in the vast majority of patients with atrial cardiomyopathy without ventricular cardiomyopathy. Finally, many anti-arrhythmic drugs used to prevent and treat AF are suboptimal (Ehrlich, Biliczki et al. 2008).

Ventricular cardiomyopathy is currently viewed predominantly from a structural perspective. Therefore, an individual's ventricular disease is tracked by repeated measurement of left ventricular ejection fraction (LVEF) or the ventricular dimension on an echocardiography. This poses several problems. First, the difference between LVEF, for example 30% versus 25%, is of unclear significance in terms of identifying symptoms, treatment, prognosis, or risk for VT/VF. Second, echocardiography or ventriculography are only reproducible for LVEF within broad ranges, and other methods such as radionuclide angiography are more cumbersome. Third, clinical practice does not show significance in day-to-day or week-to-week fluctuations in structural indices.

Current methods to predict the risk for VT/VF are non-specific. As mentioned above, the most common risk factor is the presence of reduced LVEF or heart failure symptoms. However, these methods over-detect at risk individuals by a factor of up to 18:1 (i.e. 18 individuals have to receive prophylactic ICD therapy to save one individual who will actually develop VT/VF) (Myerburg and Castellanos 2006). This method also fails to identify over 50% of all individuals who experience SCA and whose LVEF is not reduced. Thus, these criteria are suboptimal.

Rate response of ventricular action potentials at a slow heart rate (109 beats per minute—within the range expected for only mild exertion such as light walking) do not predict VT/VF. (Narayan et al, 2007): This is consistent with other art (such as U.S. Pat. Nos. 6,915,156 and 7,313,437 by Christini and colleagues) which describes methods to control cardiac alternans in action potential duration by controlling the interval separating beats. These approaches have not translated into the patient care setting.

Other methods proposed to predict VT/VF have had mixed success. Most of these methods focus on presumed reentrant mechanisms, and are indirect. These methods include detecting slow conduction in an ECG (signal averaged ECG) that may indicate a predisposition to reentry (Cain, Anderson et al. 1996a). Work by Kleiger et al. (Kleiger, Millar et al. 1987) shows that reduced 24 hour variability in the interval between heart beats ("heart rate variability") predicts VT or VF. A related method examines heart rate variability after premature beats (Schmidt, Malik et al. 1999). In a related method, abnormal innervation of the ventricle assessed using nuclear imaging may identify risk for VT/VF (Arora, Ferrick et al. 2003b). U.S. Pat. No. 4,802,481 issued to Cohen (Cohen and Smith 1989) and work by others (Smith, Clancy et al. 1988a; Rosenbaum, Jackson et al. 1994; Narayan, Lindsay et al. 1999d) describes techniques for assessing myocardial electrical instability as strictly alternate-beat fluctuations in T-wave energy (also known as "T-wave alternans"). Newer methods such as described in U.S. Pat. No. 5,555,888 issued to Brewer (Brewer and Taghizadeh 1996) and work by Marrouche et al. (Marrouche, Pavia et al. 2002), use alterations in the ventricular activation after sub-threshold current to assess the risk for VT or VF. Finally, abnormal delayed enhancement of the ventricle using magnetic resonance imaging may identify risk for VT/VF (Schmidt, Azevedo et al. 2007). For VT and VF, success has been suboptimal for tools that probe the reentry circuit with electrophysiologic study (Buxton, Lee et al. 2000), the signal-averaged ECG to examine slow conduction (Cain, Anderson et al. 1996a), and indices of repolarization including T-wave alternans (Narayan 2006a) and QT dispersion (Brendorp, Elming et al. 2001).

More recent work suggests that nervous activity/innervation can increase the risk for VT/VF (Stein, Domitrovich et al. 2005) and for AF (Patterson, Po et al. 2005). However, the mechanism linking autonomic activity with arrhythmias is unclear—particularly in humans. Of note, none of these techniques are part of implantation planning for cardioverter defibrillators (ACC/AHA/ESC 2006) or are used routinely in the clinic. All have suboptimal predictive value, and therefore tend to be more of a rough guide to risk rather than a predictive tool.

Several approaches have been described to improve ventricular cardiomyopathy. However, none of these methods work in all patient populations, and some failed to reduce VT/VF in tandem with improvements in heart failure (Bradley 2003b). Some drugs have been shown to improve ventricular function in cardiomyopathy. These include angiotensin-receptor antagonists and angiotensin receptor blockers, and beta-receptor antagonists (Poole-Wilson, Swedberg et al. 2003). However, these drugs act over years, rather than acutely.

Over the past decade, it has been shown that cardiac resynchronization therapy also improves ventricular cardiomyopathy in patients with reduced LVEF, heart failure and evidence for delayed activation between ventricles (Abraham, Fisher et al. 2002). However, it remains unclear whether cardiac resynchronization therapy itself improves the aspects of heart failure that lead to VT/VF, which is why many physicians implant an ICD in tandem with a resynchronization device (ACC/AHA/ESC 2006). Placing a pacing lead close to an arrhythmia circuit enables easier termination than if leads are remote from that location (Stevenson, Khan et al. 1993; Morton, Sanders et al. 2002a). However, current studies poorly describe methods of placing a permanent pacemaker or defibrillator lead to reduce VT/VF. Tse et al. (Xu, Tse et al. 2002), Leclercq et al. (LeClercq, Victor et al. 2000), and Meisel et al. (Meisel, Pfeiffer et al. 2001) among others, show that carefully selected ventricular pacing—particularly in the left ventricle—can improve hemodynamics and, based on work by Zagrodzky et al. (Zagrodzky, Ramaswamy et al. 2001), reduce arrhythmia incidence.

Further, it is known that pacing in certain regions of the heart, such as the right ventricle, can lead to right ventricular cardiomyopathy (DAVID 2002). However, many patients do not experience right ventricular cardiomyopathy due to pacing, and physicians still practice right ventricular pacing. However, the only way to determine if the detrimental effect is developing is to examine worsening in LVEF.

In animals, AF or atrial cardiomyopathy is not spontaneous but rather is caused by very rapid pacing or toxic drugs. In animals with experimentally induced atrial fibrillation, one can see evidence of the changes in atrial cardiomyopathy from histology or at the sub-cellular level (Ausma, van der Velden et al. 2003). However, as described above, obtaining tissue samples from human atria in human being is very difficult. Human AF is also different from AF in animal models. Therefore, there exists a need to better detect heart instability in humans.

The following references provide additional background information: Abraham, W. T., et al. (2002), "Cardiac Resynchronization in Chronic Heart Failure", *N Engl J Med.* 346: 1845-1853; ACC/AHA/ESC (2006). "ACC/AHA/ESC 2006 Guidelines for Management of Patients With Ventricular Arrhythmias and the Prevention of Sudden Cardiac Death—Executive Summary. A Report of the American College of Cardiology/American Heart Association Task Force and the European Society of Cardiology Committee for Practice Guidelines (Writing Committee to Develop Guidelines for Management of Patients With Ventricular Arrhythmias and the Prevention of Sudden Cardiac Death)", *J Am Coll Cardiol* 48(5): 1064-1108; Arora, R., et al. (2003b), "1-123 MIBG imaging and heart rate variability analysis to predict the need for an implantable cardioverter defibrillator", *Journal of Nuclear Cardiology* 10(2): 121-131; Ausma, J., et al. (2003), "Reverse Structural and Gap-Junctional Remodeling After Prolonged Atrial Fibrillation in the Goat", *Circulation* 107 (15): 2051-2058; Bloomfield, D. M., et al. (2002). "Interpretation and Classification of Microvolt T-Wave Alternans Tests", *J. Cardiovasc Electrophysiol.* 13(5): 502-512; Bradley, D. J. (2003b), "Combining Resynchronization and Defibrillation Therapies for Heart Failure", *JAMA* 289(20): 2719; Brendorp, B., et al. (2001), "QT Dispersion Has No Prognostic Information for Patients With Advanced Congestive Heart Failure and Reduced Left Ventricular Systolic Function", *Circulation* 103: 831-5; Brewer, J. E. and E. Taghizadeh, U.S. Pat. No. 5,555,888, "Method for automatic, adaptive, active facilitation to access myocardial electrical instability"; Bristow, M. R., et al. (2004), "Cardiac-Resynchronization Therapy with or without an Implantable Defibrillator in Advanced Chronic Heart Failure", *N Engl J Med* 350(21): 2140-2150; Buxton, A. E., et al. (2000), "Electrophysiologic testing to identify patients with coronary artery disease who are at risk for sudden death. Multicenter Unsustained Tachycardia Trial Investigators (MUSTT)." *N Engl J Med.* 342(26): 1937-45; Cain, M. E., et al. (1996a), "Signal-Averaged Electrocardiography: ACC Consensus Document", *J Am. Coll. Cardiol.* 27(1): 238-49; Calkins H., et al. (2007), *Heart Rhythm* 4:816-861; Chugh, S. S., et al. (2001),"Epidemiology and natural history of atrial fibrillation: clinical implications. " *J Am Coll Cardiol* 37(2):371-8; Cohen, R. J. and J. M. Smith U.S. Pat. No. 4,802,491 (1989), "Method and apparatus for assessing myocardial electrical instability"; David, D. T. I. (2002), "Dual-Chamber Pacing or Ventricular Backup Pacing in Patients With an Implantable Defibrillator: The Dual Chamber and VVI Implantable Defibrillator (DAVID) Trial", *J Am Medical Association* 288 (No. 24): 3115-3123; Ehrlich, J. R., et al. (2008), "Atrial-selective approaches for the treatment of atrial fibrillation." *J Am Coll Cardiol* 51(8): 787-92; Faddis, M. N., et al. (1999), "A Decrease in Approximate Entropy Predicts The Onset of Atrial Fibrillation" [abstract], Pacing and Clinical Electrophysiology 22(4 (part II)): 358; Franz, M. R., et al. (1988a). "Cycle length dependence of human action potential duration in vivo. Effects of single extrastimuli, sudden sustained rate acceleration and deceleration, and different steady-state frequencies", *J Clin Invest* 82(3): 972-979; Frustaci, A., et al. (1997), "Histological Substrate of Atrial Biopsies in Patients With Lone Atrial Fibrillation." *Circulation* 96(4): 1180-1184; Gold, M. R., et al. (2000a). "A Comparison of T Wave Alternans, Signal Averaged Electrocardiography and Programmed Ventricular Stimulation for Arrhythmia Risk Stratification." *J. Am. Coll. Cardiol.* 36: 2247-2253; Gong et al. (2007) *Circulation* 115: 2092-2102. [0050] Hao, S., D. Christini, et al. (2004), "Effect of beta-adrenergic blockade on dynamic electrical restitution in vivo", *Am J Physiol Heart Circ Physiol* 287(1): H390-4; Kalb, S., et al. (2004). "The restitution portrait: a new method for investigating rate-dependent restitution", *J Cardiovasc Electrophysiol* 15(6): 698-709. [0052] Kleiger, R. E., P. Millar, et al. (1987). "Decreased heart rate variability and its association with increased mortality after acute myocardial infarction", *Am. J Cardiol.* 59: 256-262. [0053] Klein, M., S. J. Evans, et al. (1995). "Use of P-wave triggered, P-wave signal-averaged electrocardiogram to predict atrial fibrillation after coronary bypass surgery." *Am. Heart J.* 129(5): 895-901; Kuo, C.-S., et al. (1983), "Characteristics and possible mechanism of ventricular arrhythmia dependent on the dispersion of action potential durations", *Circulation* 67: 1356-1367; Laurita, K. R. and D. S. Rosenbaum (2008), "Mechanisms and potential therapeutic targets for ventricular arrhythmias associated with impaired cardiac calcium cycling." *J Mol Cell Cardiol* 44(1): 31-43; LeClercq, C., F. Victor, et al. (2000), "Comparative effects of permanent biventricular pacing for refractory heart failure in patients with stable sinus rhythm or chronic atrial fibrillation", *The American Journal of Cardiology* 85(9): 1154-1156; Marrouche, et al. (2002), "Nonexcitatory stimulus delivery improves left ventricular function in hearts with left bundle branch block", *J Cardiovasc Electrophysiol* 13(7): 691-5; Meisel, E., et al. (2001), "Investigation of coronary venous anatomy by retrograde venography in patients with malignant ventricular tachycardia", *Circulation* 104(4): 442-447; Morton, J. B., et al. (2002a), "Sensitivity and specificity of concealed entrainment for the identification of a critical isthmus in the atrium: relationship to rate, anatomic location and antidromic penetration", *J Am Coll Cardiol* 39(5): 896-906; Myerburg, R. J. and A. Castellanos (2006), "Emerging paradigms of the epidemiology and demographics of sudden cardiac arrest", *Heart Rhythm* 3(2): 235-239; Narayan, S. M. (2006a), "T-Wave Alternans and The Susceptibility to Ventricular Arrhythmias: State of the Art Paper", *J Am Coll Cardiol* 47(2): 269-281; Narayan, S. M., et al. (2002b), "Alternans Of Atrial Action Potentials As A Precursor Of Atrial Fibrillation", *Circulation* 106:1968-1973; Narayan, S. M., et al., "T-wave alternans, Restitution of Ventricular action potential duration and outcome", *J Am Coll Cardiol* 2007; 50: 2385-2392; Narayan, S. M., et al. (1999d), "Demonstrating the Pro-arrhythmic Preconditioning of Single Premature Extrastimuli Using the Magnitude, Phase and Temporal Distribution of Repolarization Alternans", *Circulation* 100: 1887-1893; Narayan, S. M. and J. M. Smith (1999b), "Spectral Analysis of Periodic Fluctuations in ECG Repolarization", *IEEE Transactions in Biomedical Engineering* 46(2): 203-212; Narayan, S. M. and J. M. Smith (2000c), "Exploiting Rate Hysteresis in Repolarization Alternans to Optimize the Sensitivity and Specificity for Ventricular Tachycardia", *J. Am. Coll. Cardiol.* 35(5): 1485-1492; Patterson, E., et al. (2005). "Triggered firing in pulmonary veins initiated by in vitro autonomic nerve stimulation", *Heart Rhythm* 2(6): 624-31; Poole-Wilson, P. A., K. Swedberg, et al. (2003), "Comparison of carvedilol and metoprolol on clinical outcomes in patients with chronic heart failure in the Carvedilol Or Metoprolol European Trial (COMET): randomised controlled trial", *The Lancet* 362(9377): 7-13; Robertson, R. M. (2000, "Sudden Death from Cardiac Arrest—Improving the Odds", *N Engl J Med* 343(17): 1259-1260; Rosenbaum, D. S., et al. (1994), "Electrical alternans and vulnerability to ventricular arrhythmias", *N Engl J Med* 330(4): 235-41; Schauerte, P., et al. (2000a), "Transvenous Parasympathetic Nerve stimulation in the Inferior Vena Cava and Atrioventricular Conduction", *J. Cardiovascular Electrophysiol.* 11(1): 64-69; Scherlag, B. J., et al. (2005), "Electrical Stimulation to Identify Neural Elements on the Heart: Their Role in Atrial Fibrillation", *Journal of Interventional Cardiac Electrophysiology* 13(0):37-42; Schmidt, A., et al. (2007), "Infarct tissue heterogeneity by magnetic resonance imaging identifies enhanced cardiac arrhythmia susceptibility in patients with left ventricular dysfunction", *Circulation* 115(15): 2006-14; Schmidt, G., et al. (1999), "Heart-rate turbulence after ventricular premature beats as a predictor of mortality after acute myocardial infarction", *Lancet* 353: 1390-1396; Smith, J. M., et al. (1988a), "Electrical Alternans and cardiac electrical instability", *Circulation* 77(1):110-21; Stambler, B. S. and K. A. Ellenbogen (1996b), "Elucidating the Mechanisms of Atrial Flutter Cycle Length Variability Using Power Spectral Analysis Techniques", *Circulation* 94(10): 2515-2525; Stein, P. K., et al. (2005), "Traditional and Nonlinear Heart Rate Variability Are Each Independently Associated with Mortality after Myocardial Infarction", *Journal of Cardiovascular Electrophysiology* 16(1): 13-20; Steinberg, J. S., et al. (1994), "Use of the signal-averaged electrocardiogram for predicting inducible ventricular tachycardia in patients with unexplained syncope. Relationship to clinical variables in a multivariate analysis", *J. Am. Coll. Card.* 23: 99; Steinberg, J. S., et al. (1993a), "The value of the P-wave signal-averaged electrocardiogram for predicting atrial fibrillation after cardiac surgery", *Circulation* 88:2618; Stevenson, W. G., et al. (1993), "Identification of reentry circuit sites during catheter mapping and radiofrequency ablation of ventricular tachycardia late after myocardial infarction", *Circulation* 88: 1647-1670; Therkelsen, S., et al. (2004), "Atrial Volume and ANP in Persistent Atrial Fibrillation—Before and After Cardioversion" (abstract), *Circulation* 110(17 Suppl); Thomas, L., et al. (2002), "Compensatory changes in atrial volumes with normal aging: is atrial enlargement inevitable?", *Journal of the American College of Cardiology* 40(9):1630-1635; Wachtell, K., M. Lehto, et al. (2005), "Angiotensin II receptor blockade reduces new-onset atrial fibrillation and subsequent stroke compared to atenolol: The Losartan Intervention For End point reduction in hypertension (LIFE) study", *Journal of the American College of Cardiology* 45(5): 712-719; Walker, et al. (2003), "Hysteresis Effect Implicates Calcium Cycling as a Mechanism of Repolarization Alternans", *Circulation* 108 (21): 2704-2709; Watanabe, K., et al. (1980), "Computer Analysis of the Exercise ECG: A Review", *Prog. Cardiovasc. Dis.* 22(6): 423-446; Weiss, J. N., et al. (2006). "From Pulsus to Pulseless: The Saga of Cardiac Alternans (Review)", Circ Res 98: 1244; Xu, W., et al. (2002), "New Bayesian Discriminator for Detection of Atrial Tachyarrhythmias", *Circulation* 105: 1472-1479; Zagrodzky, J. D., et al. (2001), "Biventricular pacing decreases the inducibility of ventricular tachycardia in patients with ischemic cardiomyopathy", *Am J Cardiol* 87(10): 1208-1210.

SUMMARY OF THE INVENTION

In one embodiment, a method of diagnosing the onset of heart instability comprises monitoring signals from a beating human heart, detecting one or a combination of oscillations in the signal shape, oscillations in the signal duration or changes in signal characteristics in response to changes in rate or beat irregularity; and assigning a risk for heart instability based at least in part on the detecting.

In another embodiment, a method of treating the potential onset of heart instability comprises monitoring signals from a beating human heart, detecting one or a combination of oscillations in the signal shape, oscillations in the signal duration or changes in signal characteristics in response to changes in rate or beat irregularity, modifying tissue structure and/or function, detecting attenuated oscillations and/or changes in signal characteristics in response changes in rate and/or beat irregularity.

In another embodiment, an apparatus for diagnosing and treating heart instability comprises one or more sensors configured to detect signals from a beating human heart, means for detecting one or a combination of oscillations in the signal shape, oscillations in the signal duration or changes in signal characteristics in response to changes in rate or beat irregularity, means for assigning a risk for heart rhythm irregularities based at least in part on the detecting, and means for modifying tissue structure and/or function based at least in part on the detecting.

In another embodiment, an apparatus for creating a risk assessment for heart rhythm irregularities comprises at least one sensor, an analytic engine comprising a module configured to measure a signal received via the at least one sensor, a module configured to measure a rate-response of the signal at a plurality of rates, and a module configured to produce and/or change a determined risk for heart rhythm irregularities based at least in part on the rate-response measurement.

In another embodiment, a method of assessing risk and/or time onset for atrial fibrillation comprises monitoring electrical signals representing cellular action potentials from an atrial chamber of a beating human heart, determining a slope of an action potential restitution curve, detecting fluctuations in signal amplitude or duration, detecting conduction slowing, and assessing risk and/or time onset for atrial fibrillation based at least in part on the determining and detecting.

DETAILED DESCRIPTION OF THE PREFERRED EMBODIMENTS

Figure 1A:
FIGS. 1A-1C illustrate monophasic heart action potential signals that may be analyzed according to certain embodiments.

Detailed descriptions of certain embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the embodiments in virtually any appropriately detailed system, structure or manner. Before moving on to specific details, certain aspects of certain embodiments of the invention are presented below.

Embodiments of methods and systems for treating heart or possibly other organ instability are disclosed herein. In accordance with one embodiment, there is disclosed a method to create an index of health and disease computed from fluctuations in a biologic signal. The index of health or disease may pertain to components of an organ. The signal may comprise many types.

Certain embodiments comprise an apparatus to measure the biological signal with sufficient fidelity to detect small variations. The apparatus may perturb the biological signal. The apparatus may attenuate the index of disease and thus improve health.

Certain embodiments may include a method to create an index of health and disease computed from fluctuations in a biologic signal including one or more of the following: wherein said index measures the periodicity, amplitude and phase of oscillations in the signal over time; wherein said oscillations are repetitive; wherein said oscillations do not repeat; wherein said signal oscillations vary after a perturbation; wherein the perturbation is altered activation rate or sequence; wherein the perturbation is altered activation of the autonomic nervous system; wherein the perturbation is modification of tissue structure; wherein the perturbation is modification of tissue function (behavior); wherein said signal oscillations measure biochemical changes in the organ cells responsible for disease; wherein said biochemical changes are fluctuations in calcium; wherein said biochemical changes are fluctuations in potassium; wherein said biochemical changes are fluctuations in metabolic components; wherein said index measures variations of said signal between regions of the organ or within the body; wherein variations over time are measured from activations of components of an organ; and wherein the organ is the heart.

In certain embodiments, the index of health or disease pertains to components of an organ. Some of the embodiments may include one or more of the following: wherein said index of health or disease pertains to components of an organ; wherein the organ is the heart; wherein the components are the atria; wherein the components are the ventricles; wherein disease refers to cardiomyopathy; wherein disease refers to rhythm disorders; wherein disease refers to coronary artery disease; wherein rhythm disorders include atrial tachycardia, atrial fibrillation, ventricular tachycardia or ventricular fibrillation; wherein disease refers to medication side-effects; wherein health refers to absence of cardiomyopathy; wherein health refers to absence of heart rhythm disorders; wherein health refers to improved autonomic nervous system regulation; wherein health refers to improved hormonal regulation; wherein health refers to effectiveness of therapy; wherein therapy is cardiac device therapy; wherein therapy is transplantation; wherein the organ is smooth muscle, such as in the gastrointestinal or respiratory systems; wherein the organ is skeletal muscle; wherein the organ is the brain.

In certain embodiments, the biological signal comprises one or more of the following: an intracellular or extracellular action potential wherein variations pertain to the shape, wherein variations pertain to the duration, and/or wherein variations pertain to the amplitude; a monophasic action potential; an organ electrogram, wherein variations pertain to activation, wherein variations pertain to repolarization, and/or wherein variations pertain to diastole; an electrocardiogram wherein variations pertain to the QRS and T-waves, wherein variations pertain to the QT interval, wherein variations pertain to the ST segment, and/or wherein variations pertain to the TP segment; a magnetocardiogram wherein variations pertain to the QRS and T-waves, wherein variations pertain to the QT interval, represents conduction time between regions of the organ, and/or wherein conduction slows for certain perturbations; a measure of tissue motion, wherein variations measure wall motion on echocardiography, wherein variations measure wall motion on tissue Doppler imaging, and/or wherein variations pertain to the echocardiographic displacement of the atrioventricular ring.

In certain embodiments, the biological signal indicates one or more of the following: functioning of the central nervous system; functioning of the respiratory system; functioning of the urogenital system; functioning of the gastrointestinal system; functioning of smooth muscle; functioning of skeletal muscle.

Other embodiments may include an apparatus to measure the biological signal with sufficient fidelity to detect small variations, the apparatus comprising: a sensor; noise-reduction and filtering apparatus; means of transmitting said signal using physical media, as electrical signals along wires or within body fluid; means of transmitting said signal wirelessly; an apparatus to analyze the signal to construct said index; an apparatus to communicate the said index to the health care provider and patient; wherein the sensor is in contact with the organ; wherein the sensor is a pacing lead; wherein the sensor is elsewhere in the body but not in contact with the organ; wherein the sensor does not contact the body and remotely measures said signal.

Certain embodiments may include an apparatus to perturb said biological signal comprising: means for altering the rate of activation of the organ; means for altering the sequence (regularity or irregularity) of activation of the organ; means for altering autonomic nervous control of the organ; wherein the autonomic nervous control is of the atria of the heart; wherein the autonomic nervous control is of the ventricles of the heart; means for altering hormonal influences of the organ; and means for altering biochemical equilibrium in the organ.

Certain embodiments may include an apparatus to attenuate said index of disease, prevent onset of the heart instability and thus improve health, the apparatus including one or more of the following: means for increasing or decreasing activation rate if said index is found to be dependent upon heart rate; means for altering the pattern of activation of the organ, based on said index; wherein the new pattern enables cellular processes to normalize; wherein the new pattern includes slow activations for cellular processes to regain equilibrium; wherein the new pattern includes fast activations to achieve a desired average heart rate; wherein the new pattern attenuates disease-forming oscillations to prevent the disease onset; wherein the new pattern is non-regular; wherein the new pattern is regular; means for modifying tissue structure, such as by ablation; means for modifying tissue function, such as by using an external electrical field; means for modifying autonomic nervous regulation of the organ by altering the structure or function or nerves; wherein the nerves alter functioning in the heart atria; wherein the nerves alter functioning in the heart ventricles; wherein the nerves alter functioning in the gastrointestinal tract; wherein the nerves are in the central nervous system; wherein the nerves alter functioning in the urogenitary system; wherein the nerves alter functioning in the respiratory system.

Biological systems require many checks and balances to ensure stability and health of the individual. These checks and balances are implemented by complex regulatory systems. Although many potentially serious diseases arise if these systems fail, few methods exist in humans to detect impending failure of these systems to diagnose disease at an early stage, to guide therapy, or to track its effectiveness. Systems and methods are described herein that may detect impending failure of such regulatory systems and, in the process, predict and prevent disease.

Without being bound to any particular theory of operation, the inventor has recognized that AF and VT/VF may start from subtle cellular metabolic abnormalities, rather than clear structural disease. Fundamentally, the failure of the arrhythmia prediction tools utilized to date may stem from their inability to accurately or consistently detect these abnormalities. Thus, in some embodiments, it is postulated that subtle abnormalities in cell functioning can be uncovered to diagnose disease at an early stage. Methods and systems of treatment are described which attenuate abnormalities and prevent the onset and the progression of disease (e.g. in the atrium and/or the ventricle), including the onset of heart rhythm instability.

As described herein, the inventor has found that AF is linked with oscillations and abnormal rate-behavior of atrial action potentials in humans. The inventor has also linked VT/VF with oscillations and abnormal rate-behavior of ventricular action potentials in humans. These signals can indicate impending failure of cell-functions such as regulation of intracellular calcium, which is linked to the eventual failure of mechanical function (cardiomyopathy) and electrical function (heart rhythm disorders). Certain embodiments thus detect risk at an earlier stage and also guide effective therapy to stabilize such oscillations and prevent disease.

It has also been found by the inventor that nervous activation predisposes humans to arrhythmias (atrial and ventricular) by altering cell-level mechanisms which cause fluctuations or abnormal rate-behavior of action potentials. Thus, certain embodiments are based on the inventor's recognition that these fluctuations represent the abnormal cellular handling of calcium or other biochemicals. The abnormal cellular handling of calcium or other biochemicals has been seen to indicate arrhythmias in canines and other animal studies (Patterson, Po et al. 2005), but has not previously been shown in humans. Over time, this imbalance may worsen which explains progressive cardiomyopathy (increasing atrial size) and an increasing risk for AF. Thus, certain embodiments described herein detect failure in the cellular regulation of calcium, and thus potential atrial cardiomyopathy (heart failure), in the beating heart of patients by tracking the underlying failure of regulation mechanisms.

Abnormal cellular calcium regulation due to ventricular cardiomyopathy may also explain VT or VF onset. Certain embodiments, therefore, measure fluctuations in heart electrical (or mechanical) signals to probe the failure of regulatory mechanisms underlying VT/VF. In certain embodiments, treatment can also be provided to attenuate fluctuations and suppress VT/VF, and certain such embodiments can then track the effectiveness of this and other treatments.

The physiological basis of the detection methods described herein can be described with reference to FIGS. 1A-7C which provide example signals and signal characteristics that can be analyzed in some embodiments of the invention. As described further below, a wide variety of signal types can be analyzed in accordance with the principles of the invention, and the specific embodiments below are merely exemplary.

Figure 1B:
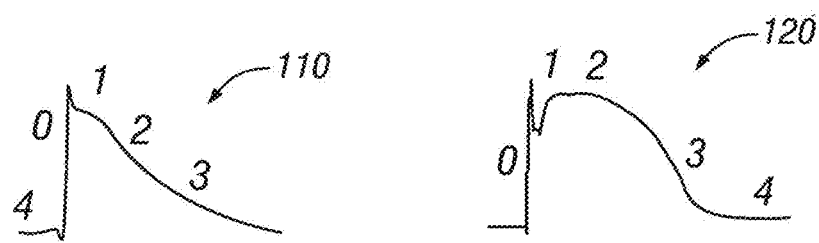

FIG. 1A illustrates a series of human action potential (AP or MAP) signals 105 recorded from a location in a human ventricle. FIG. 1B shows two individual action potentials recorded from a location in the left atrium 110 and a location in the left ventricle 120 respectively. Each action potential has phases 0, 1, 2, 3 and 4. Phases 0-1 indicate depolarization and phases 2-3 indicate repolarization. Phase 4 indicates the time interval from one beat to the next. In certain embodiments, the rate response (restitution) of one or more components may be determined, focusing on rate-response of AP duration (time from phase 0-3) and AP phase 2 amplitude.

Figure 1C:
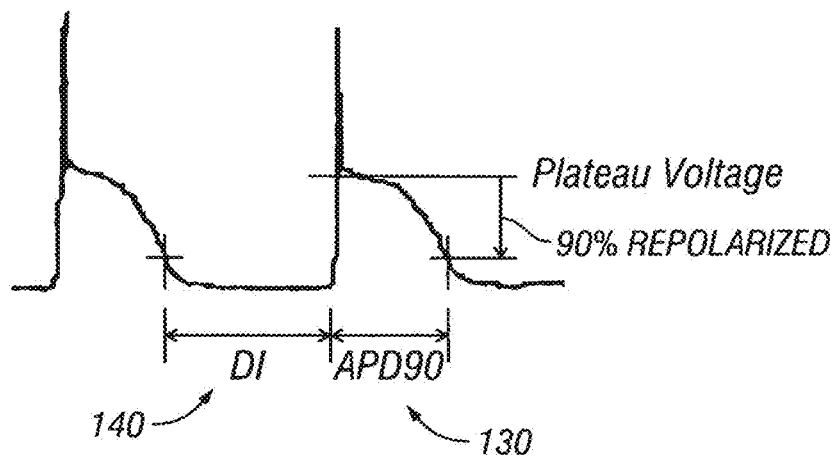

FIG. 1C illustrates various signal characteristics of action potentials that can be analyzed to indicate cellular events and thus predict propensity for AF and VT/VF. For example, for action potentials, the time taken from onset of the action potential (phase 0) to the time of 90% repolarization from the plateau phase (near the end of phase 3) designated 130 in FIG. 1C is termed APD90. The diastolic interval 140 is the time from the APD point of the prior beat to the initiation of the beat in question. In various embodiments of the invention, any repolarization phase can be used (for instance, APD70, APD80), and so the term APD will be used herein to refer to any and all of these repolarization phases. In addition, certain surrogates may be used to measure repolarization phases. Some surrogates may better correlate with certain repolarization phases; in particular, unipolar electrogram activation recovery intervals correlate well with APD90 (Yue, Paisey and coworkers, Circulation 2004). Rate response characteristics of the AP biosignal and their relationship to arrhythmias are illustrated in FIGS. 2A-7C.

Figure 2A:
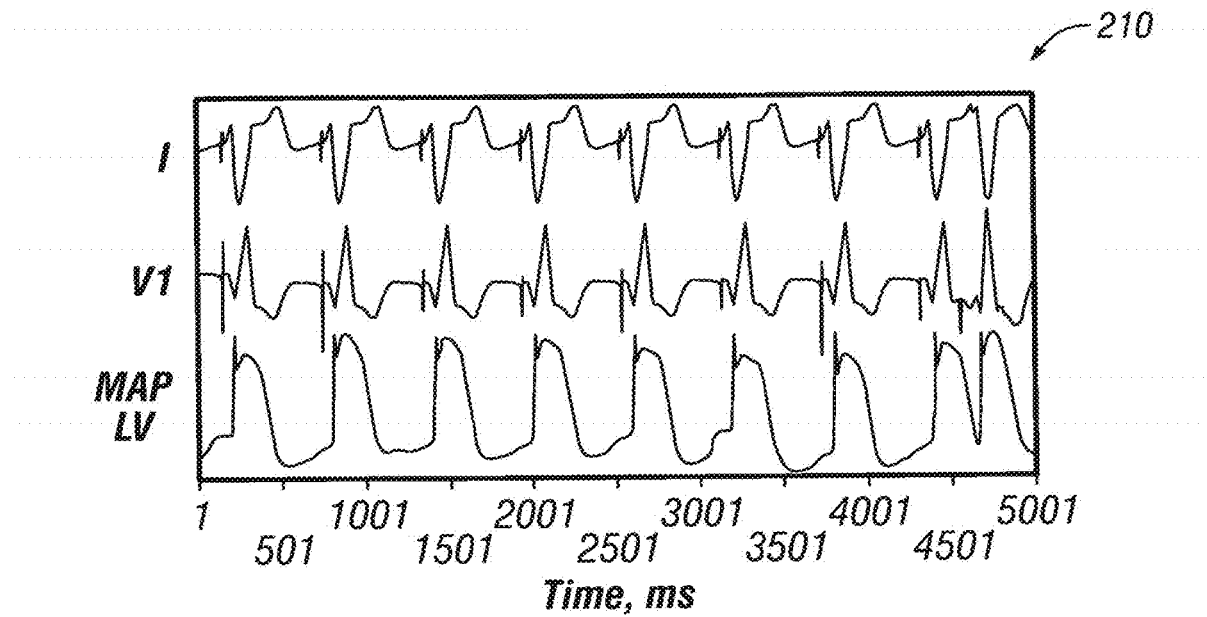
FIGS. 2A-2B illustrate one embodiment of analyzing human ventricular action potential signals to compute a rate-behavior (restitution) curve.
Figure 2A:
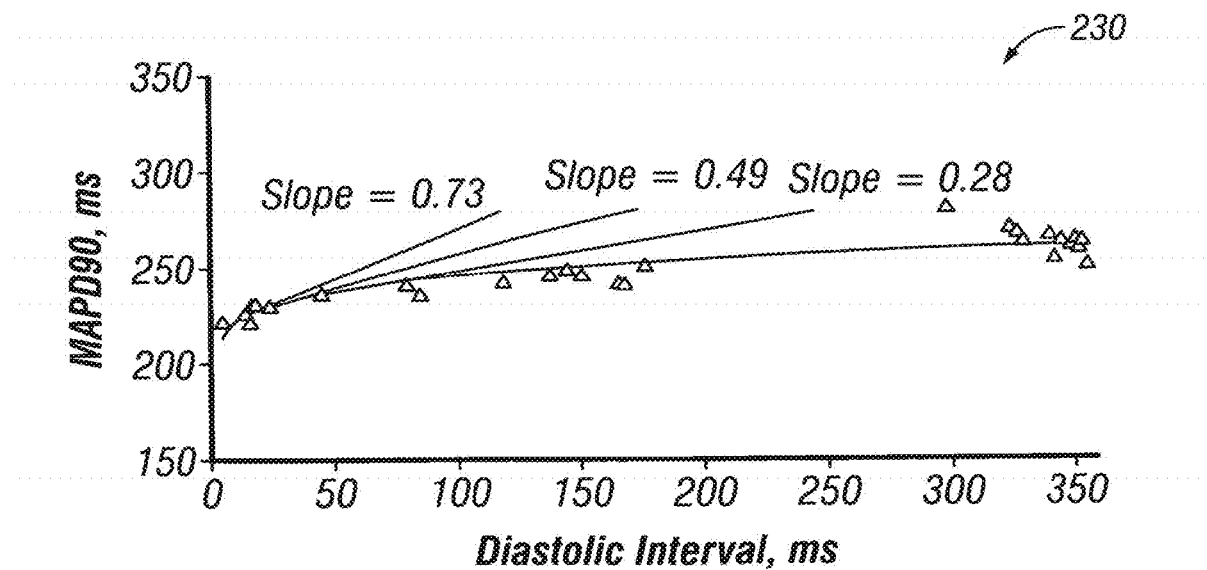
Figure 2B:
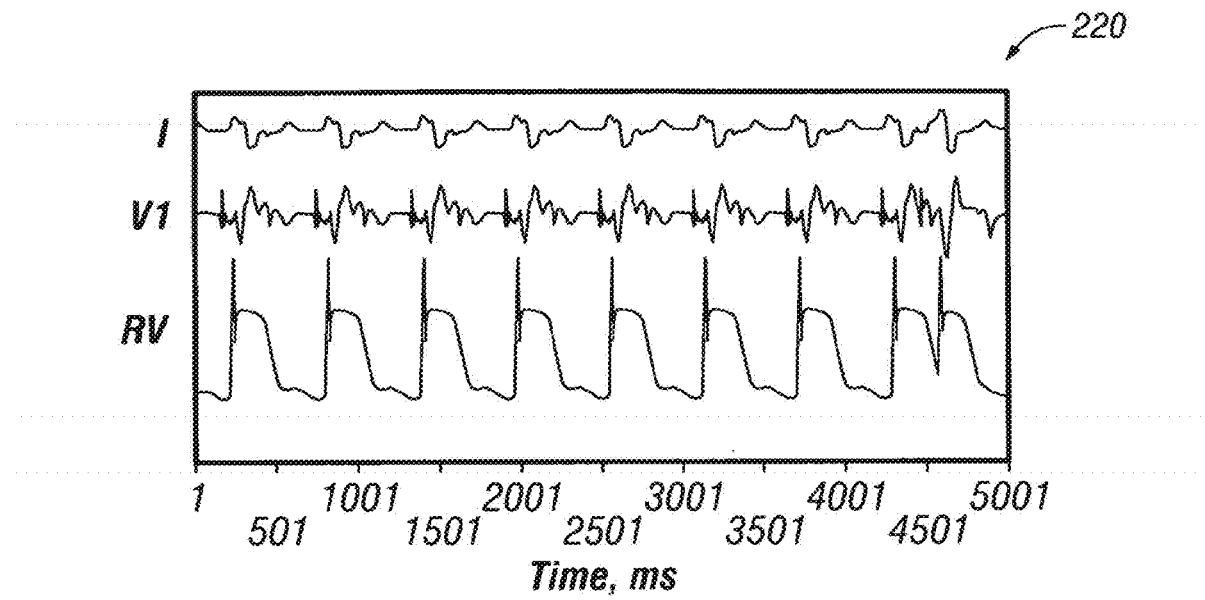
Figure 2B:
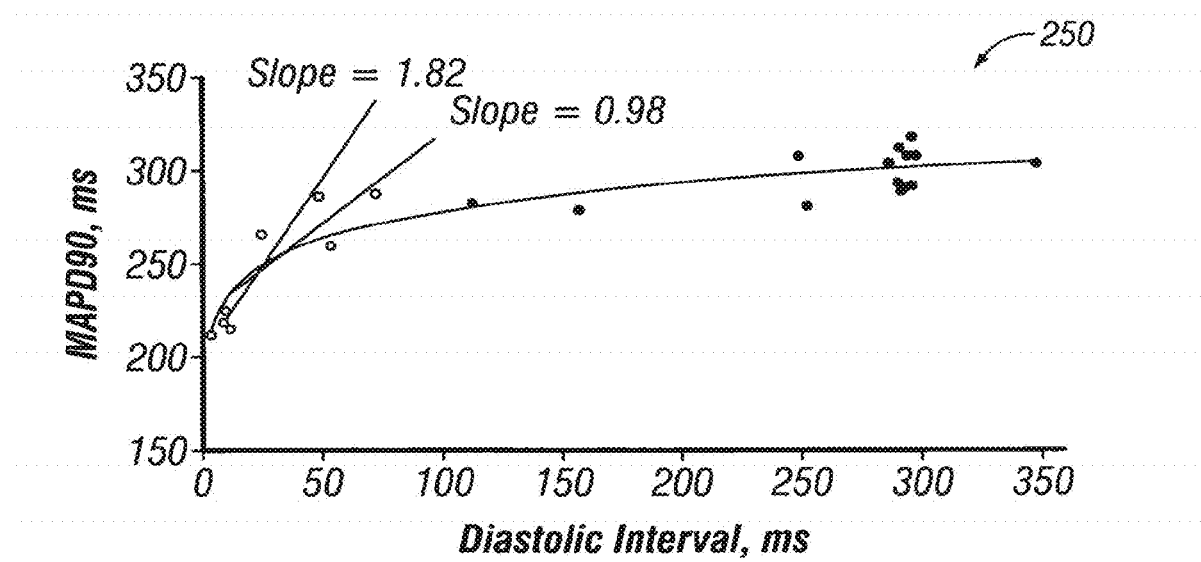

FIGS. 2A and 2B illustrate one embodiment of analyzing human ventricular signals to compute a rate-behavior (restitution) curve. FIGS. 2A and 2B illustrate ventricular action potentials, although analysis may be analogous for any biosignal. In both FIGS. 2A and 2B, the top panels 210 and 220 respectively each illustrate for two different subjects a series of regular beats of the heart then an early beat. These panels thus illustrate a beat irregularity in that the interval between beats is not constant over the time of observation. To analyze these signals, action potentials are separated, and each measured to determine diastolic interval and APD as shown in FIG. 1C.

Bottom panels 230 and 250 respectively illustrate the rate response (restitution) curves for APD for these two subjects. The rate-behavior (restitution) curve is traditionally plotted as the APD (vertically) against the preceding diastolic interval separating one beat from the next (shown in item 140). The illustrated restitution curve is created from early beats (as in panels 210, 220), but can also be created during any rate variations, such as variations in heart rate between rest (slow), minimal exertion (moderate range rate) and maximal exertion (fastest rate).

The APD restitution curve is conventionally described by several parameters, including its maximum slope (illustrated in items 230, 250), range between minimum and maximum APD and the longest diastolic interval for which slope is greater than 1. It has been shown in animals, but never before in humans, that maximum APD restitution slope >1 predicts spontaneous arrhythmias. For example, the individual associated with the data in FIG. 2A had maximum APD restitution slope <1, and did not experience arrhythmias on follow-up. The individual associated with FIG. 2B had APD restitution slope >1 and did experience arrhythmias. Notably, restitution (rate response) can be measured for any signal component, such as upstroke velocity (phase I, sodium channel functioning), plateau voltage (phase II, sodium, calcium and other channel functioning), duration (phase III/IV, calcium and potassium channel function), and fluctuations in diastole (between action potentials) that may indicate disequilibrium in a variety of cell components.

Figure 2C:
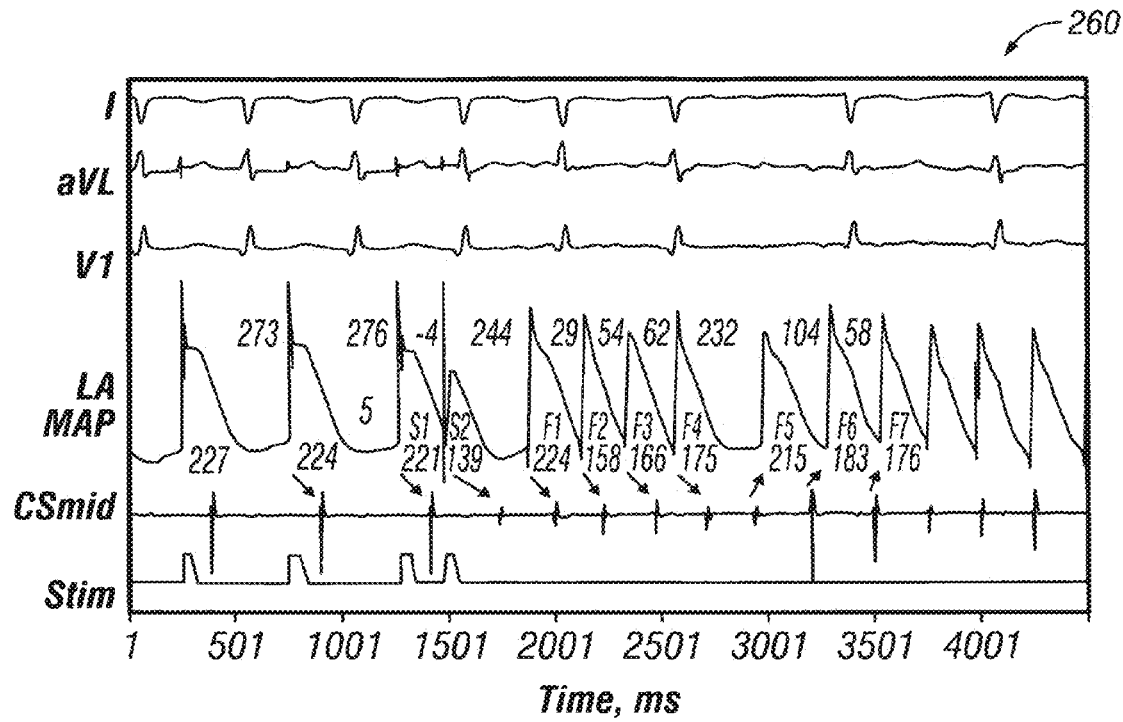
FIG. 2C illustrates the direct relationship between steep atrial rate-behavior (restitution) of action potentials, and immediate onset of atrial fibrillation in a human subject.
Figure 2C:
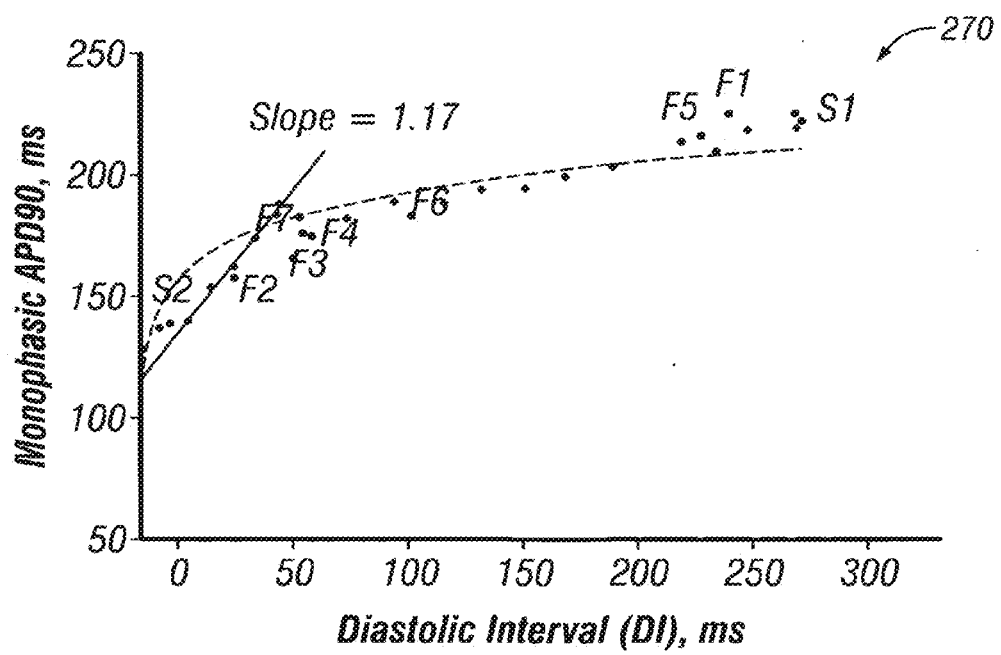

FIG. 2C illustrates atrial action potential restitution from a human patient with minimal structural disease who has paroxysmal AF. This shows the direct relationship between steep atrial rate-behavior (restitution) of action potentials, and immediate onset of atrial fibrillation in a human subject. Panel 260 shows that a single premature beat (S2) initiates AF (beats labeled F1-F7) in the patient. The APD for each beat, and its preceding diastolic interval, is shown. Notably, extreme APD oscillations are seen leading to wavebreak and AF. Panel 270 illustrates how steep APD restitution in this patient results from extreme oscillations from beat S1 to S2 to F1, F2, F3 and so on in AF. This further validates the importance of steep atrial restitution in causing human AF.

Figure 3A:
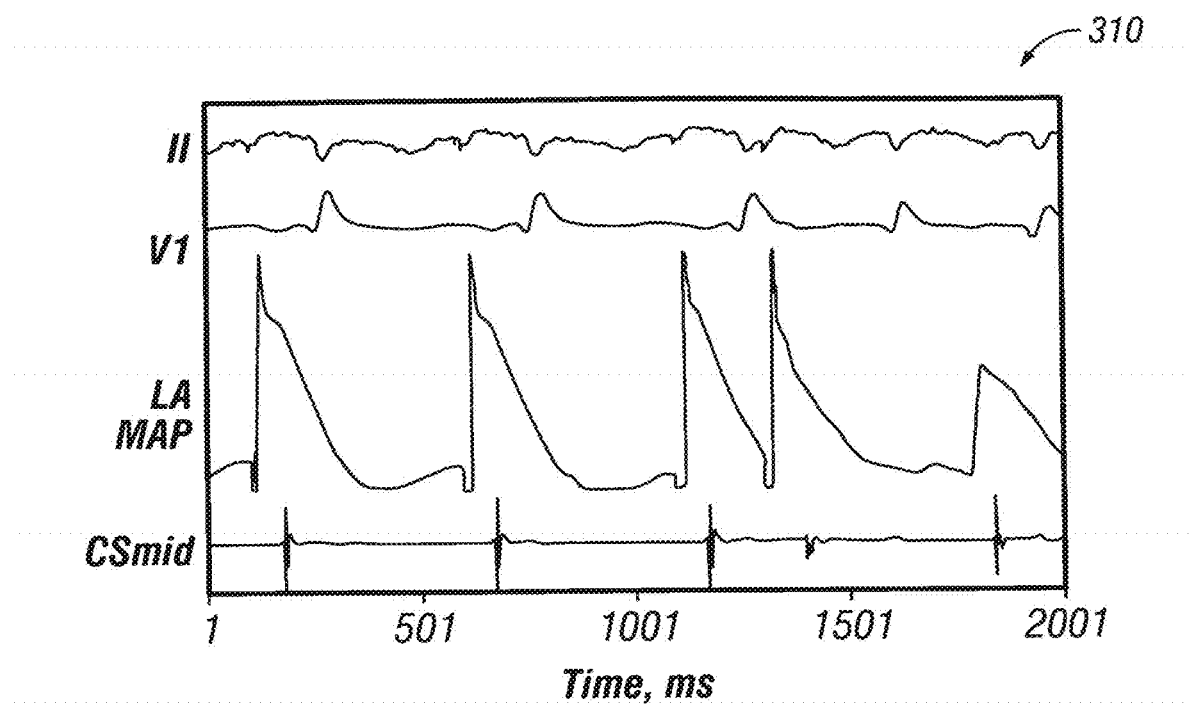
FIGS. 3A-3B illustrate one embodiment of analyzing human atrial signals to compute a rate-behavior (restitution) curve.
Figure 3A:
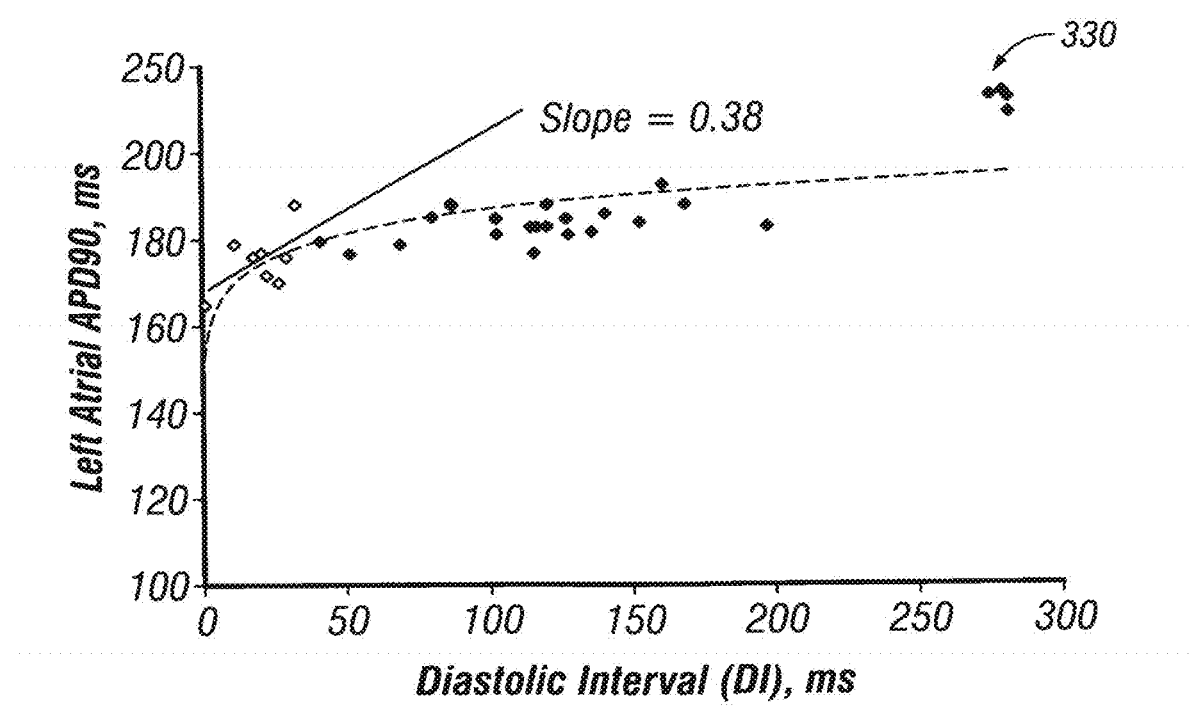
Figure 3B:
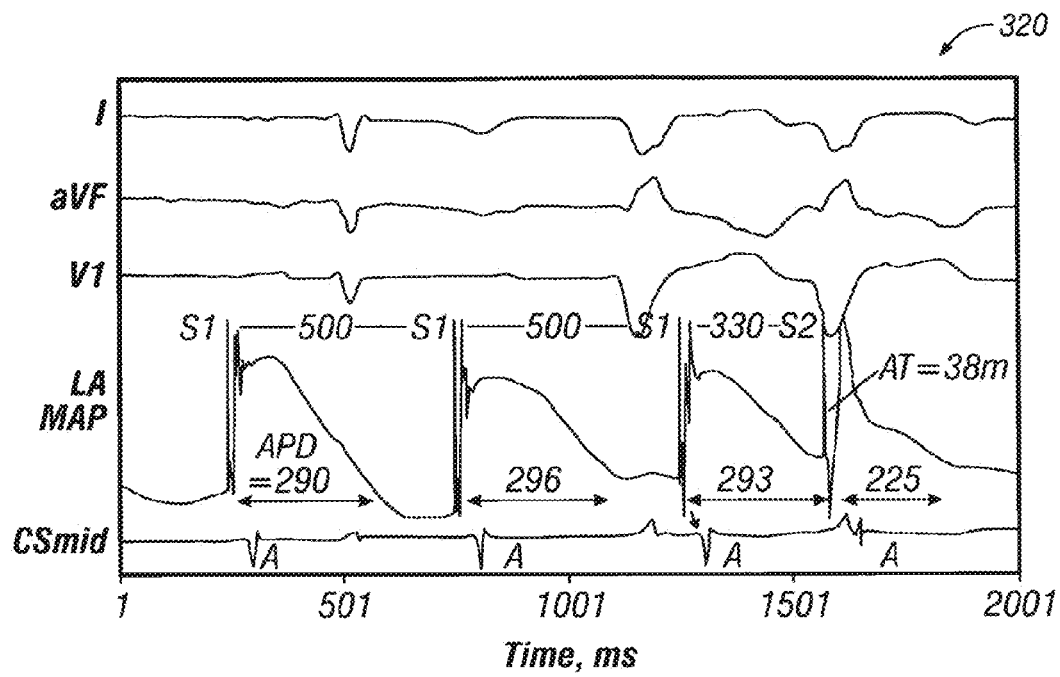
Figure 3B:
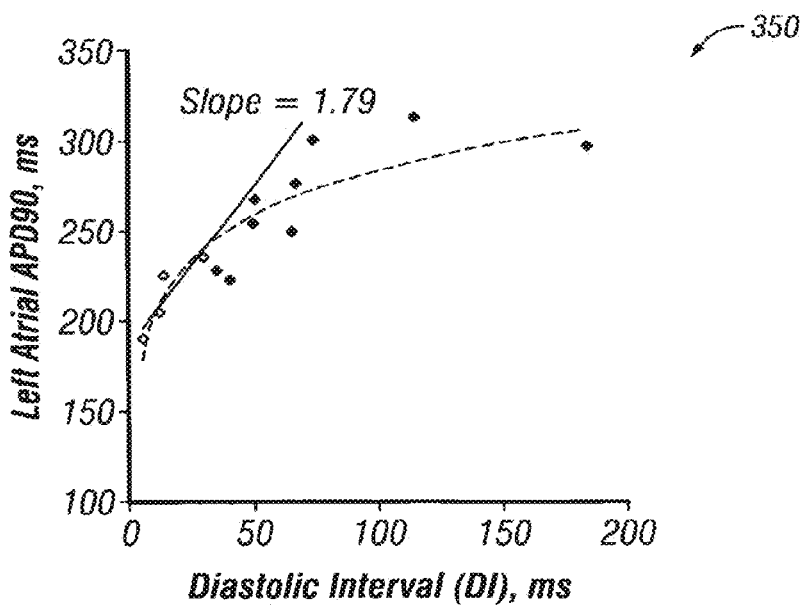

FIGS. 3A and 3B illustrate another example of analyzing human atrial signals to compute a rate-behavior (restitution) curve. Top panels 310 and 320 show a series of atrial beats then an early beat. The signal illustrated in FIG. 3A was obtained from a subject that had no AF history. The signal illustrated in FIG. 3B was obtained from a subject that had paroxysmal AF. For both signals, action potentials are measured and parsed as before (FIG. 1C, FIGS. 2A-2C).

Lower panels 330 and 350 show the rate response (restitution) curves for APD for these subjects. Again, the rate-behavior (restitution) curve is plotted as the APD (vertically) against the diastolic interval separating one beat from the next. As above, the illustrated restitution curve is created from early beats (as in panels 310 and 320), but can also be created from beat-to-beat variations between rest (slow rates), minimal exertion (moderate rates) and maximal exertion (fastest rates). The restitution curve is described by several parameters, including its maximum slope, the range between maximum and minimum APD, and the longest diastolic interval for which slope is greater than 1.

The individual in FIG. 3A is a control subject with no AF, whose maximum APD restitution slope <1. The individual in FIG. 3B did experience AF and had APD restitution slope >1.

Figure 4:
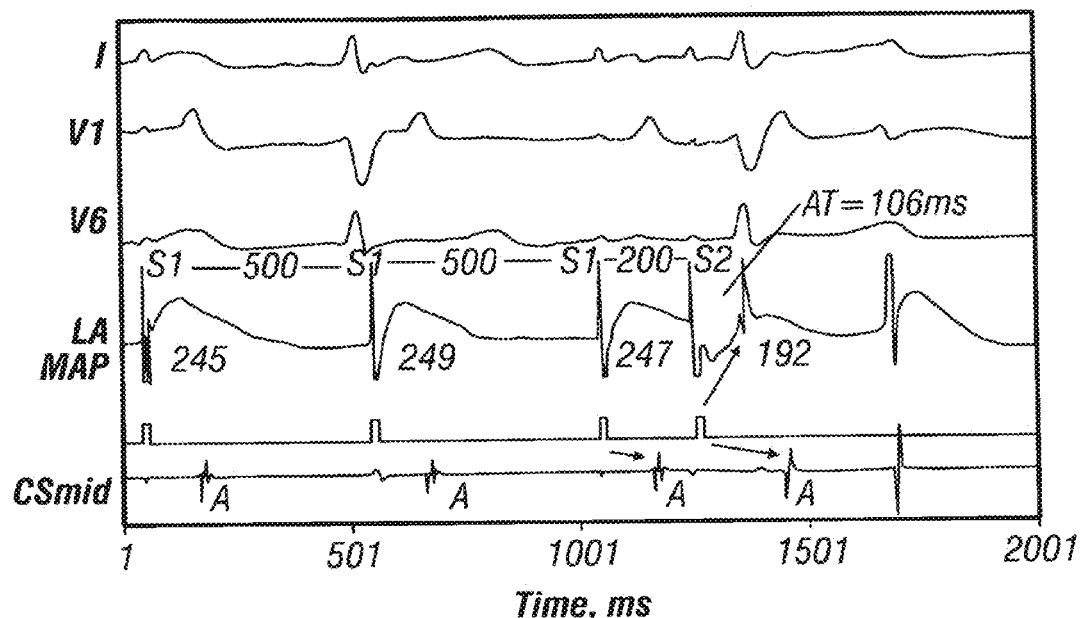
FIG. 4 illustrates one embodiment of analyzing human heart signals for dynamic (rate-related) conduction slowing, when beats are early (and have short diastolic intervals)
Figure 4:
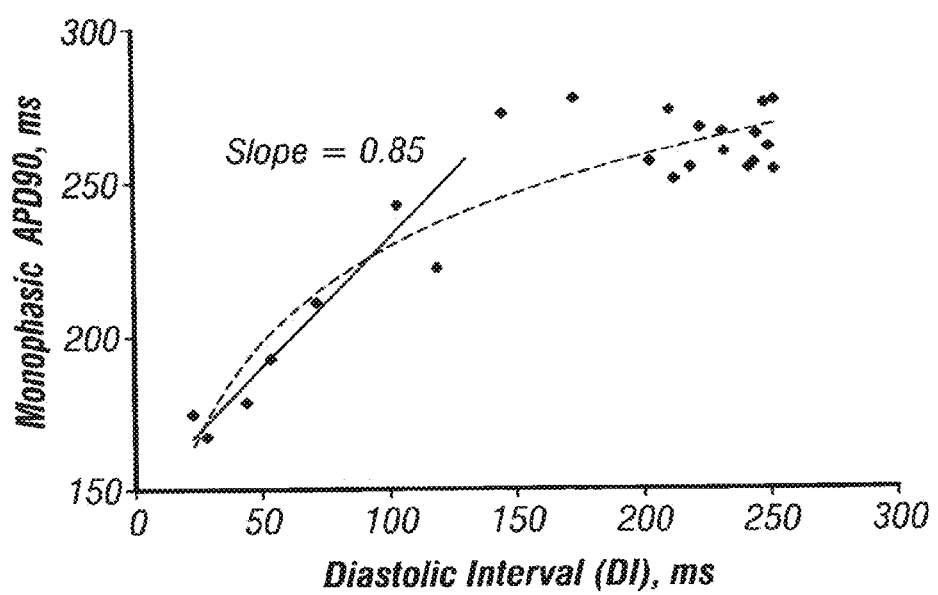

Interestingly, FIG. 4 shows an individual with longstanding AF and conduction slowing on extra beats. This delayed the actual timing of the early beat, thus truncating the left portion of the APD restitution curve and producing slope <1. This may be the reason that it has never before been shown in human atria that APD restitution slope >1 identifies patients who will develop AF. Because conduction slowing in subjects with longstanding AF has masked recognition of the correlation, the inventor is the first to utilize this relationship in human diagnosis and treatment.

Figure 5A:
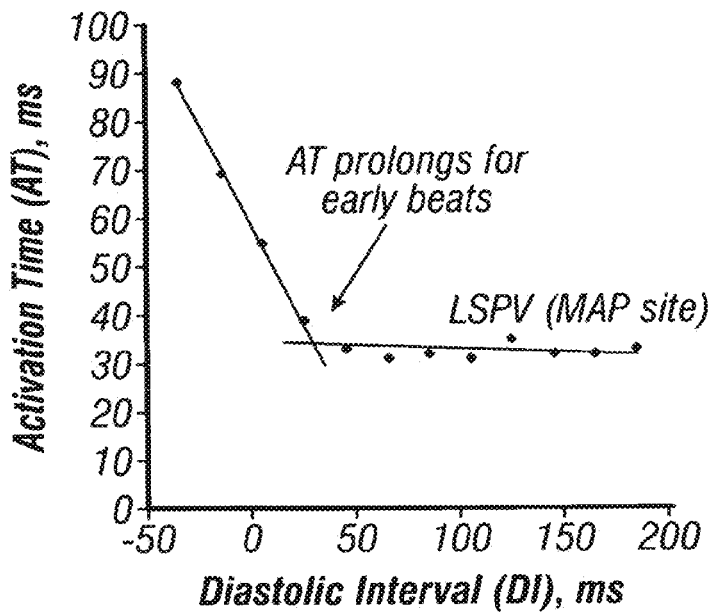
FIGS. 5A and 5B further illustrate rate-related conduction slowing, again most prominent for early beats (short diastolic intervals).
Figure 5A:
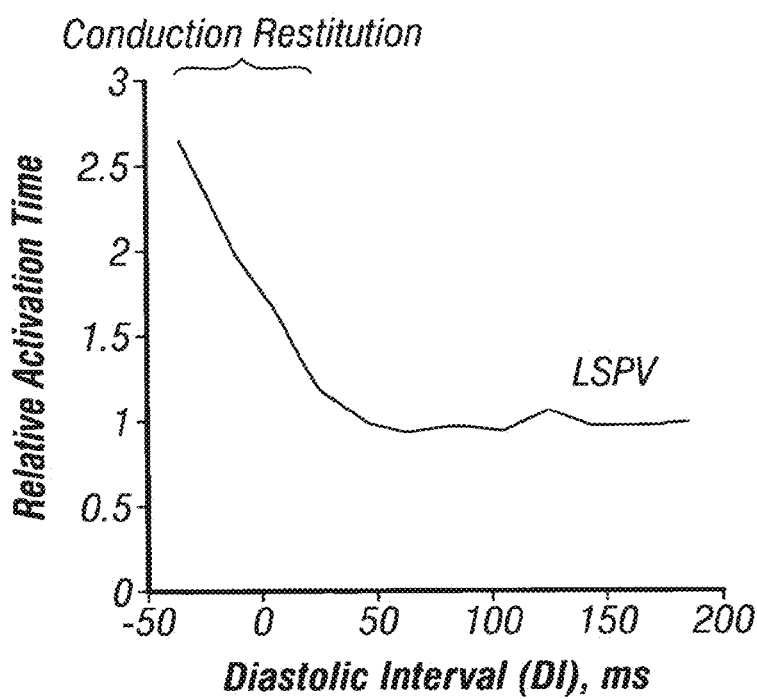
Figure 5B:
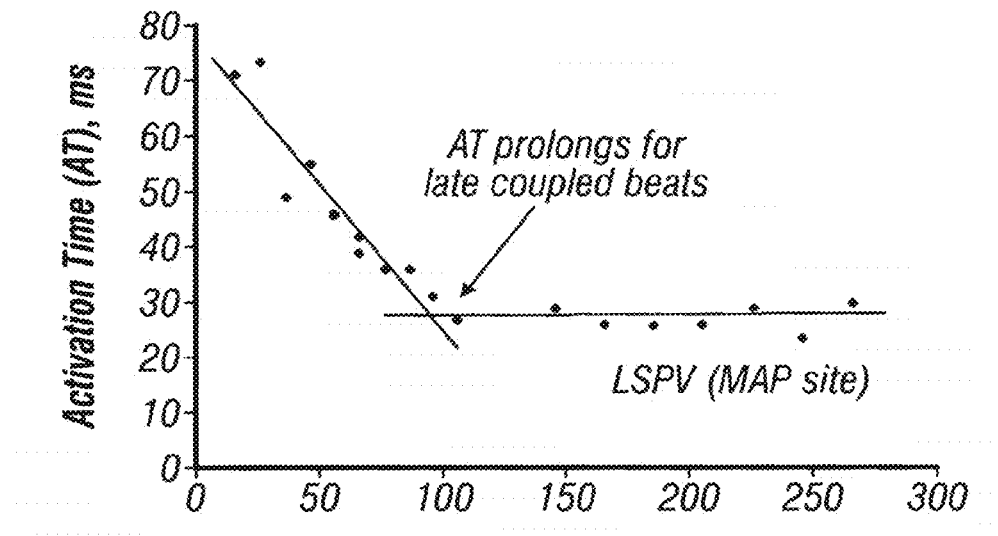
Figure 5B:
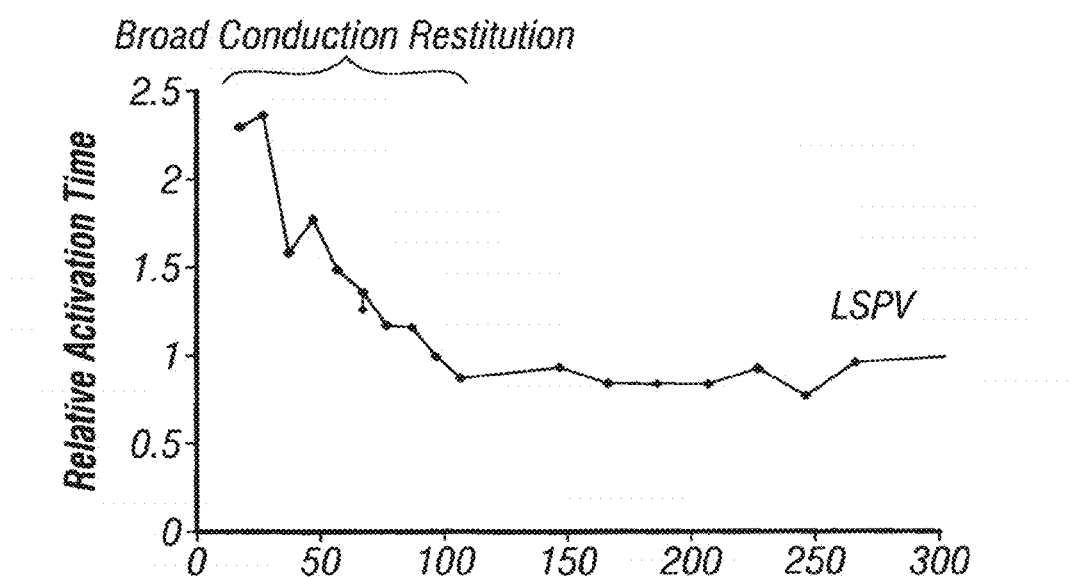

The effect of conduction slowing is illustrated further in FIGS. 5A and 5B. FIGS. 5A and 5B illustrate one embodiment of analyzing human heart signals for dynamic (rate-related) conduction slowing. The effect of conduction slowing on interpretation of results obtained from restitution analysis is described with respect to this Figure. FIG. 5A shows that conduction slowing (prolonged activation time) in subjects with early stage (paroxysmal) AF occurs only for very early beats (with very short diastolic intervals). It is relatively difficult to uncover such slowing. This is similar to predictions from computer models (Gong, et al. 2007), but has never previously been observed in the atria of humans. Conversely, FIG. 5B shows that, in a subject with longstanding advanced AF, conduction slows even for less-early beats (or relatively slow rates, with long diastolic intervals). In other words, conduction slowing is observed more easily. Accordingly, conduction slowing explains observed APD restitution flattening in patients with persistent AF (atrial cardiomyopathy)—in which conduction delay for the earliest beats truncates the leftmost portion of the APD rate-behavior (restitution) curve.

In addition to APD rate behavior, the inventor has also found that beat to beat fluctuations or oscillations in MAP wave shape (such as phase II amplitudes) can also be predictive of arrhythmias.

Figure 6:
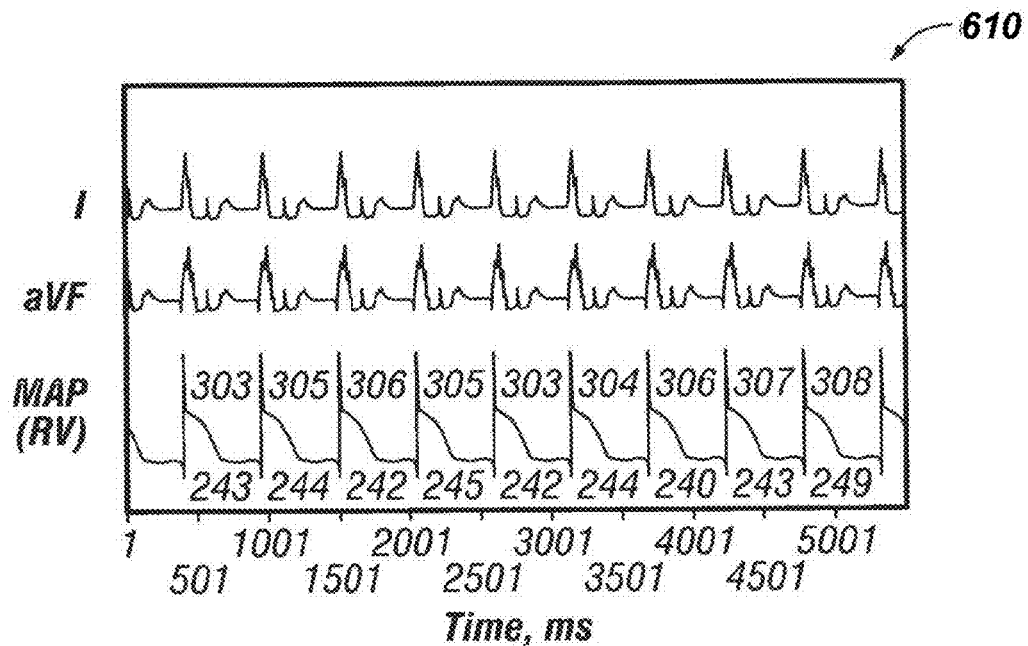
FIG. 6 illustrates fluctuations/oscillations in human ventricular signals (action potentials) in a human subject who later developed ventricular arrhythmias after many months.
Figure 6:
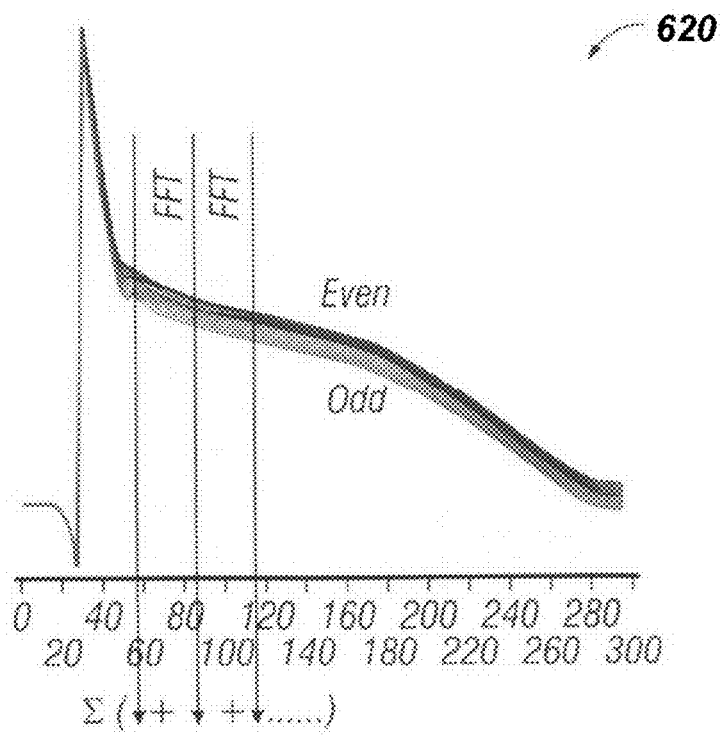
Figure 6:
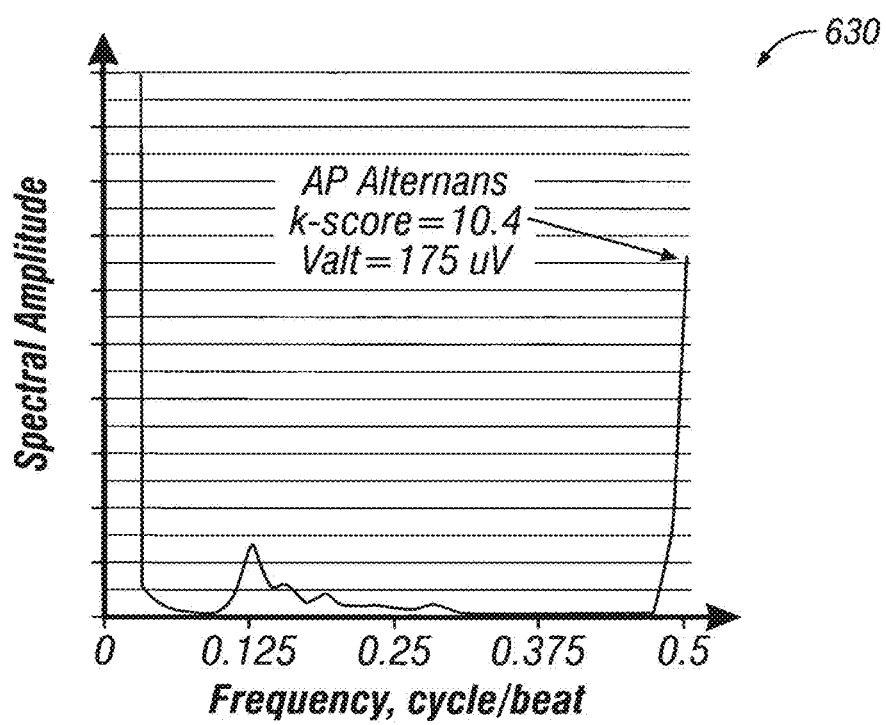

FIG. 6 illustrates fluctuations in human ventricular signals (action potentials) in a human subject who later developed ventricular arrhythmias after many months. These examples of fluctuations in human action potentials mechanistically precede and thus predict arrhythmias. As described below, baseline corrected biosignals may be used first.

In FIG. 6, panel 610 shows ventricular action potentials in a human subject who went on to develop potentially lethal ventricular arrhythmias. In panel 620, these action potentials were aligned as described below. As can be seen, the even beats (coded blue) and odd beats (coded red) segregate based on shape. In other words, there are beat-to-beat fluctuations that alternate in this case (alternans; other patients may demonstrate fluctuations on a third-beat basis or with some other periodicity). Although this can be quantified visually, spectral decomposition as illustrated by use of a fast Fourier transform (FFT) provides reproducible quantification.

Panel 630 of FIG. 6 illustrates a spectral analysis of the action potentials of panel 610. In this case, 64 contiguous APs were selected, baseline corrected to the mean of a 10 ms segment starting 20 ms prior to phase 0 maximum dV/dt, and aligned to their upstroke (phases 0-1) (Narayan and Smith 1999b). Successive APs were represented as 2-D matrices R (n, t), where n indicates beat number ($0 \leq n \leq 63$), and t the time sample (Narayan and Smith 1999b). A Fast Fourier Transform (FFT) was used to compute power spectra across beats (arrow-wise in FIG. 1C) for each t, and then spectra were summated for portions of the AP. Spectral AP fluctuations magnitude was represented by the dimensionless k-score:

$$\frac{\sum T - \mu_{noise}}{\sigma_{noise}},$$

where $\Sigma T$ is spectral magnitude at 0.5 cycles/beat, and $\rho_{noise}$ and $\sigma_{noise}$ are the mean and SD of noise, respectively. The noise window was selected adjacent to alternans frequency (0.33-0.49 Hz) to avoid the 0.125-0.25 Hz respiratory peak (Narayan and Smith 1999b). A k>0 indicates that the magnitude of fluctuations (which may represent alternans) exceeds noise (Bloomfield, Hohnloser et al. 2002). The mean voltage of alternation $V_{alt}$ across the AP duration (also referenced to the noise floor) was estimated as:

$$\sqrt{\frac{\sum T - \mu_{noise}}{AP \text{ duration}}} \text{ (in } \mu V\text{).}$$

Panel 630 shows the resulting frequency spectrum, where alternate-beat fluctuations result in a peak at a frequency of half-the-heart-beat. The inventor has further noted that the above described action potential fluctuations correlate strongly with T-wave alternans on the surface ECG. As stated above, this patient developed serious ventricular arrhythmias some months later. Data from Narayan and Smith (Narayan and Smith 2000c) and Walker and Rosenbaum (Walker, Wan et al. 2003) provide strong evidence that such fluctuations represent calcium fluctuations.

Figure 7A:
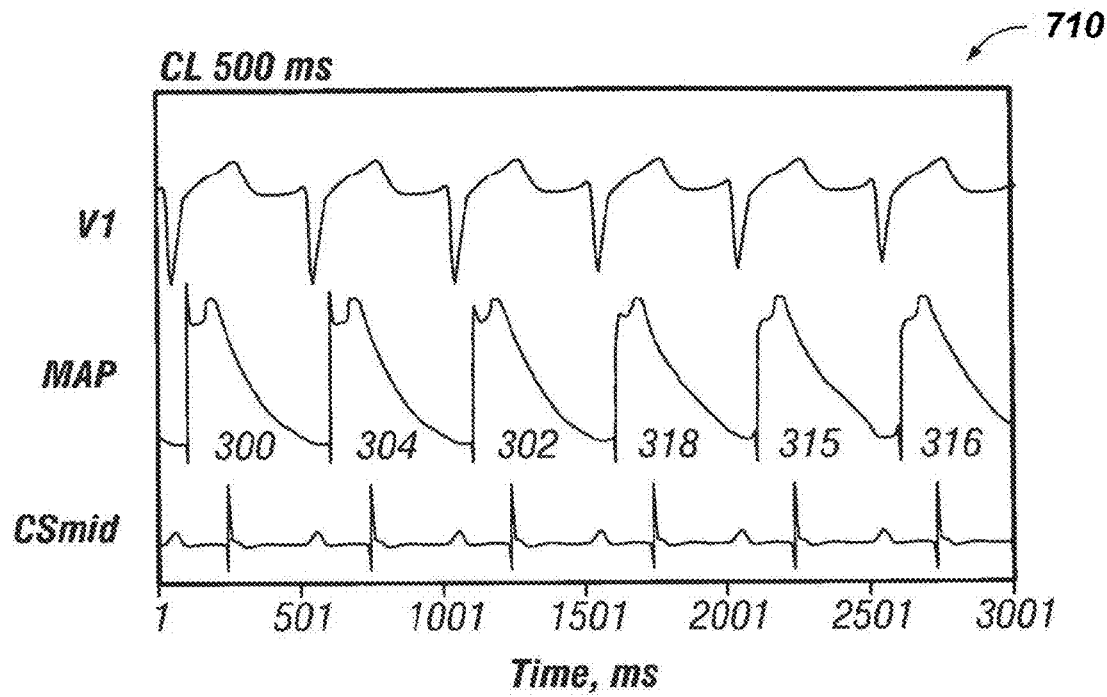
FIGS. 7A-7C illustrate rate-related fluctuations/oscillations in human atrial signals (action potentials) in a human subject who was largely without symptoms but who subsequently developed atrial fibrillation.
Figure 7A:
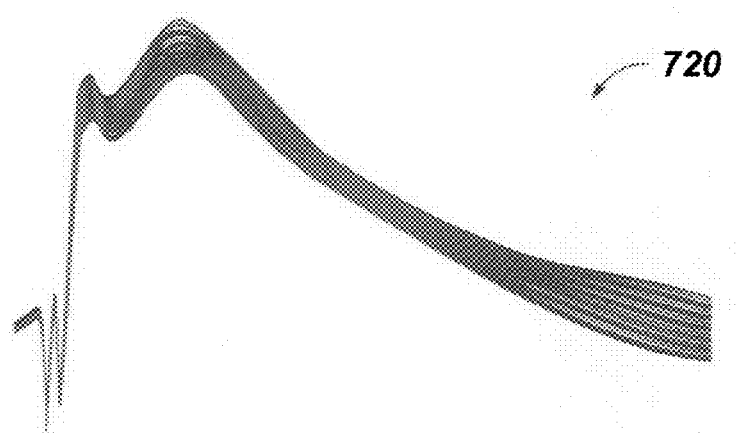
Figure 7A:
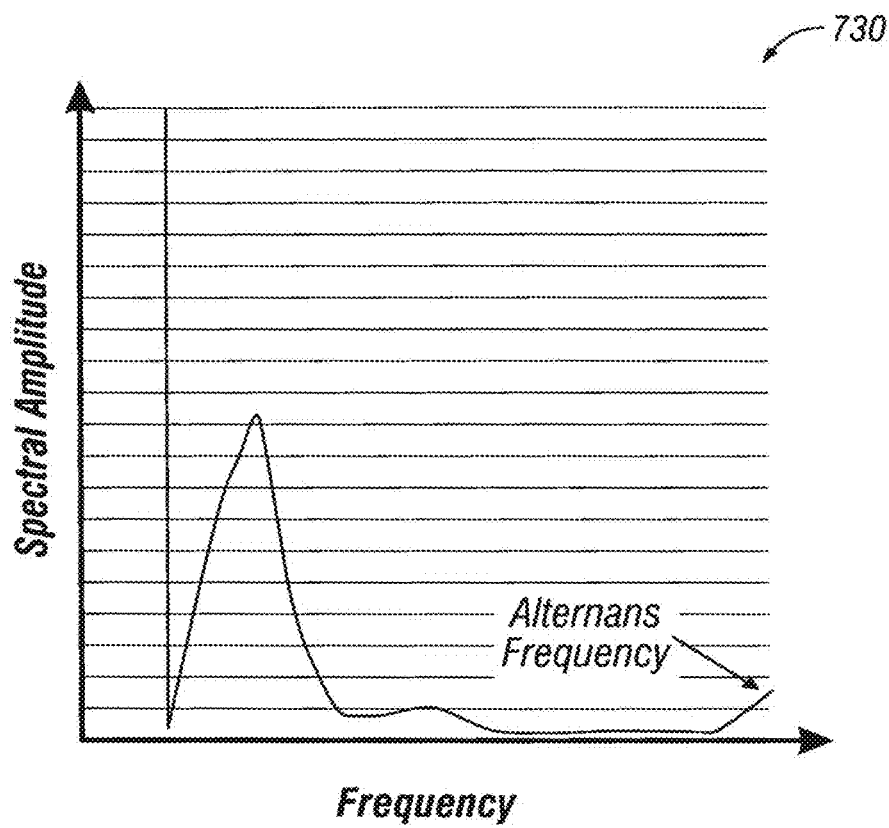
Figure 7B:
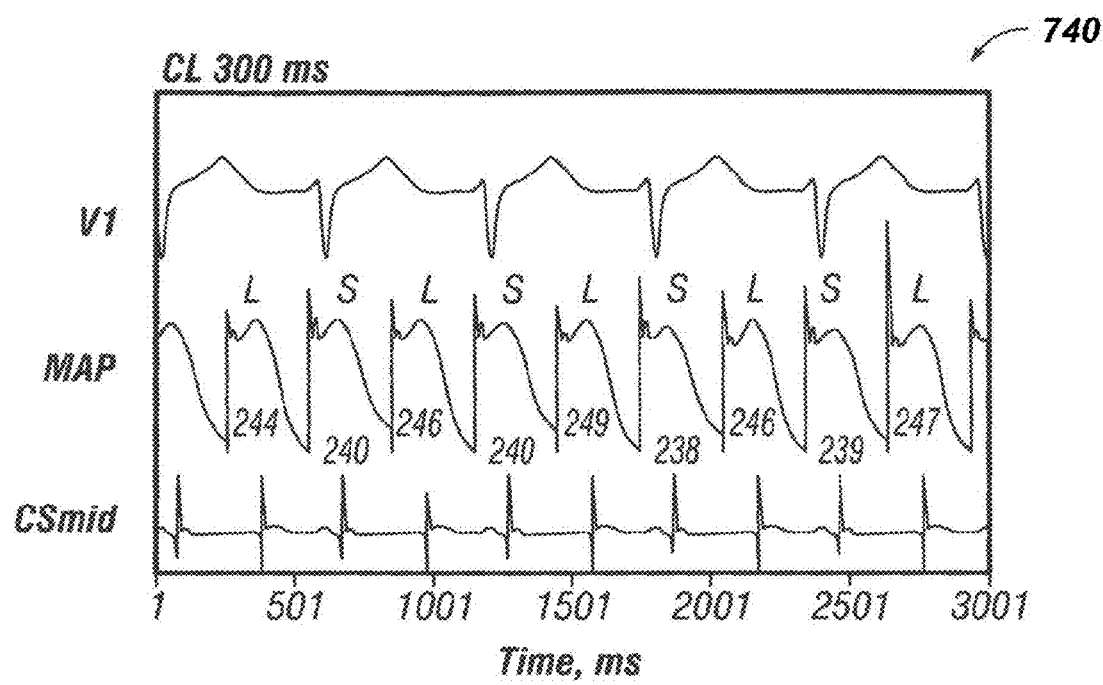
Figure 7B:
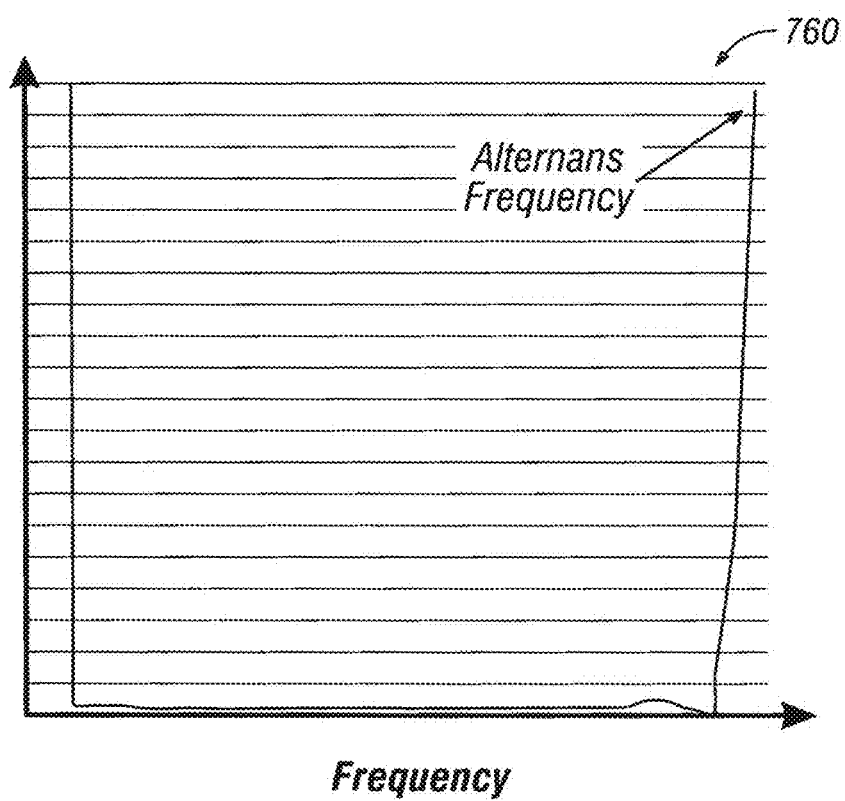
Figure 7C:
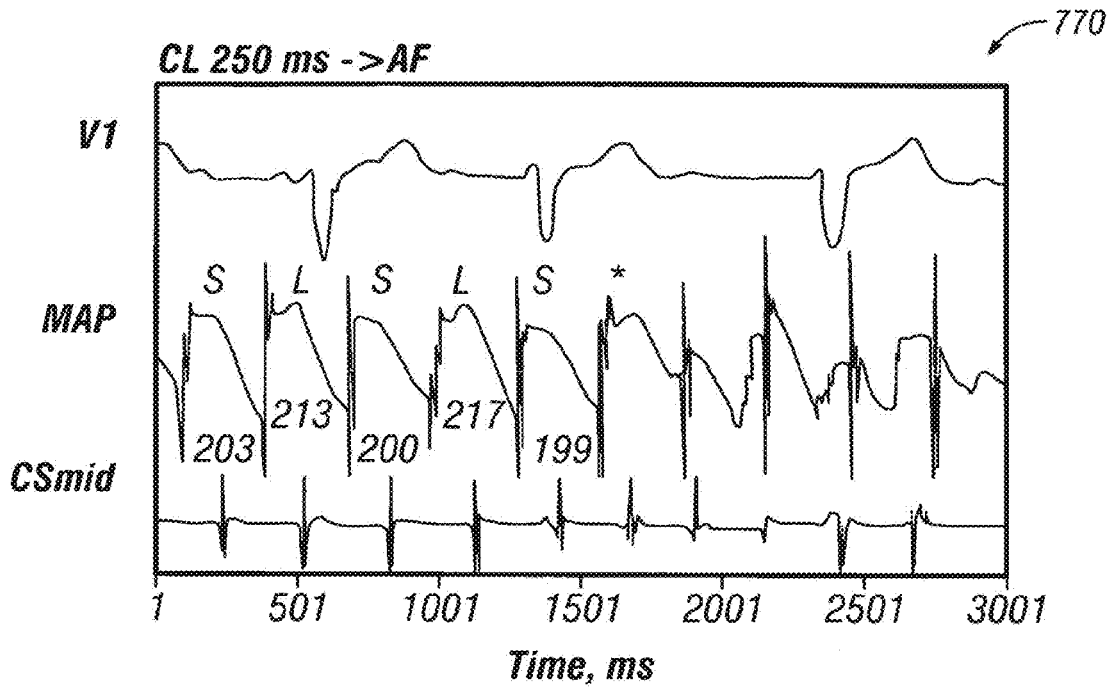
Figure 7C:
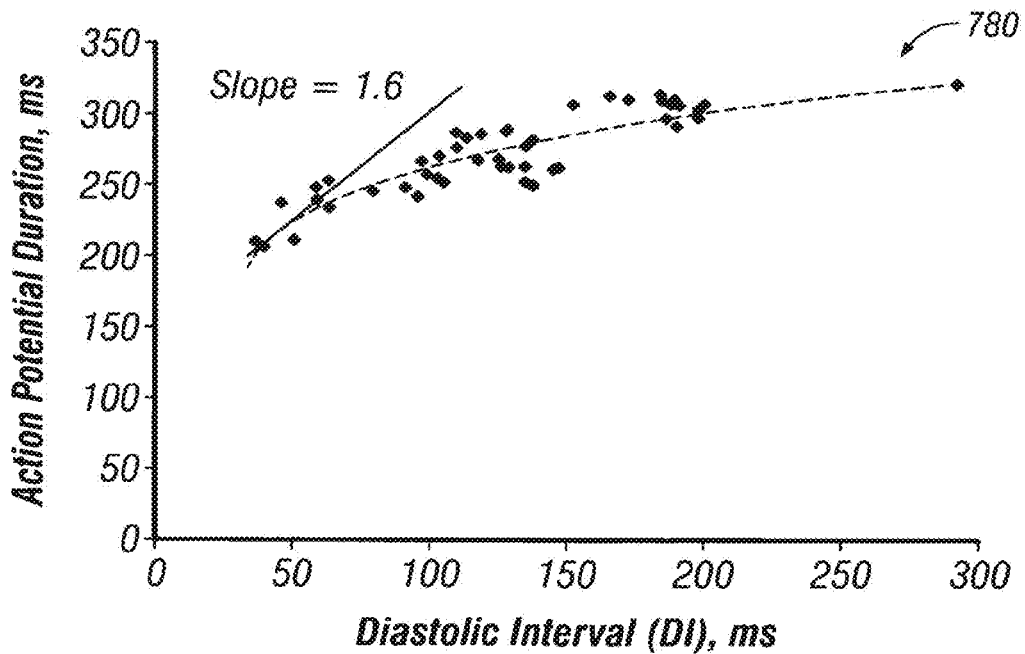

FIGS. 7A-7C illustrate fluctuations in human atrial signals (action potentials) in a human subject who was largely without symptoms but who subsequently developed atrial fibrillation. With this subject, oscillations in atrial signals are seen which increase with progressively faster pacing prior to the onset of AF. Panel 710 of FIG. 7A shows atrial action potentials during slow pacing. Panel 720 of FIG. 7A shows the aligned (red/blue) beats superimposed as described above. Minimal fluctuations are visible, although spectral analysis (FIG. 7A, panel 730) reveals small fluctuations (in this case, alternating fluctuations).

FIG. 7B illustrates signals from the same subject at faster heart rates. At faster rates (panel 740), fluctuations are visible (indicated as Short (S), Long (L), but also seen in dome amplitude). In panel 750, aligned beats are separated into red and blue groups, and spectral analysis (FIG. 7B, panel 760) reveals marked oscillations.

As shown in FIG. 7C, fluctuations can be dramatic prior to AF onset (panel 770). Panel 780 shows that this patient had APD restitution slope >1 (although this is not seen in all patients). Notably, some patients may have electrical fluctuations at slow rates, which may represent cellular calcium abnormalities.

The relationship of disease risk to rate-response (restitution) is complex. In the absence of significant structural disease, a restitution slope >1 may cause signal oscillations and predict/cause disease. However, in the presence of cellular and/or structural disease, mechanisms such as conduction slowing are involved in the initiation and maintenance of disease and add complexity to the relationship with restitution slope. These factors are summarized below in a risk score table for atrial fibrillation; similar risk score tables can be constructed for ventricular rhythm disorders with analogous elements.

| RISK SCORE TABLE FOR ATRIAL FIBRILLATION | | | | | |
|---|---|---|---|---|---|
| Structural Disease? | APD Rest Slope | Fluctuation (Alternans) | CV Slowing? | Diagnosis | Risk |
| No | <1 | No | Only for v. early beats | Minimal atrial disease | Low |
| No | <1 | Yes (at fast rates only) | Only for v. early beats | Minimal atrial disease | Low |
| No | >1 | Yes (at fast rates) | Only for v. early beats | Paroxysmal AF (early disease) | Medium. AF at fast rates |
| Yes | <1 | No | Yes | Consistent with Aging | Low to medium. |
| Yes | <1 | Yes (at slow or fast rates) | Yes | Persistent AF | High |
| Yes | >1 | Yes (at many rates) | No | Persistent AF with high adrenergic tone | High |

The embodiments of risk score assessment described herein differ from current methods. For example, the observation that alternans of atrial intracardiac signals predict the onset of AF (Narayan, Bode et al. 2002b) has only been shown in the right atrium and only in patients with pre-existing atrial flutter whose rhythms transitioned to AF. Systems and method described herein may measure fluctuations which represent cellular abnormalities, and may be detected at slow rates. These measured fluctuations may better predict arrhythmia initiation than shown in studies by others (Narayan, Bode et al. *Circulation* 2002b).

These principles allow for an unparalleled method for identifying AF risk. In some embodiments, these methods use human electrical signals that directly measure cellular pathophysiology, rather than associations (such as age, left atrial diameter and so on (Chugh, Blackshear, *J Am Coll Cardiol.* 2001). As described, the input signals may be monophasic action potentials, but can be approximated from other clinical signals such as unipolar or bipolar signals with sufficient contact pressure with the heart chamber. In addition, signals can be derived from any clinical electrode, catheter, or pacemaker lead.

The embodiments described herein are different from frequency analysis of electrograms, such as shown in work by Stambler et al. (Stambler and Ellenbogen 1996b). Those authors used FFT to analyze frequency components constituting the entire waveform. Conversely, embodiments of methods described herein use FFT to document beat-to-beat variability on a second beat, third beat (and so on) basis. Much of the current studies, such as U.S. Pat. Nos. 6,064,906 issued to Langberg, and 6,178,347 issued to Olsson, also do not disclose use of FFT in this fashion. Furthermore, the embodiments described herein may examine beat-to-beat fluctuations and thus exclude the confounding effects of subharmonic and harmonic frequencies.

Certain embodiments additionally provide a novel means of detecting the basis for T-wave fluctuations, and more specifically T-wave alternans (an ECG tool to predict lethal ventricular arrhythmias described in U.S. Pat. Nos. 4,802,491 issued to Cohen and 5,148,812 issued to Verrier). The presence of T-wave alternans predicts the presence of VT substrates in several studies by Gold et al. (Gold, Bloomfield et al. 2000a), a review by Narayan et al and others (Narayan 2006a). T-wave alternans may reflect signal fluctuations from within the heart, which may also reflect calcium oscillations. Thus, detecting such fluctuations such as described above with respect to certain embodiments, likely provides a more robust method of predicting future arrhythmias than T-wave alternans.

The above Figures illustrate biosignal analysis for early detection of potential arrythmias. Another aspect of the invention focuses on stabilization of abnormal measured cell regulation detected by cardiac fluctuations and/or large fluctuations in the biological signal such as changes in rate. In these embodiments, slower pacing rates or rhythm perturbations may be used which may help regain equilibrium in cellular handling of calcium and/or other biochemicals. This is illustrated in FIGS. 8 and 9.

Figure 8:
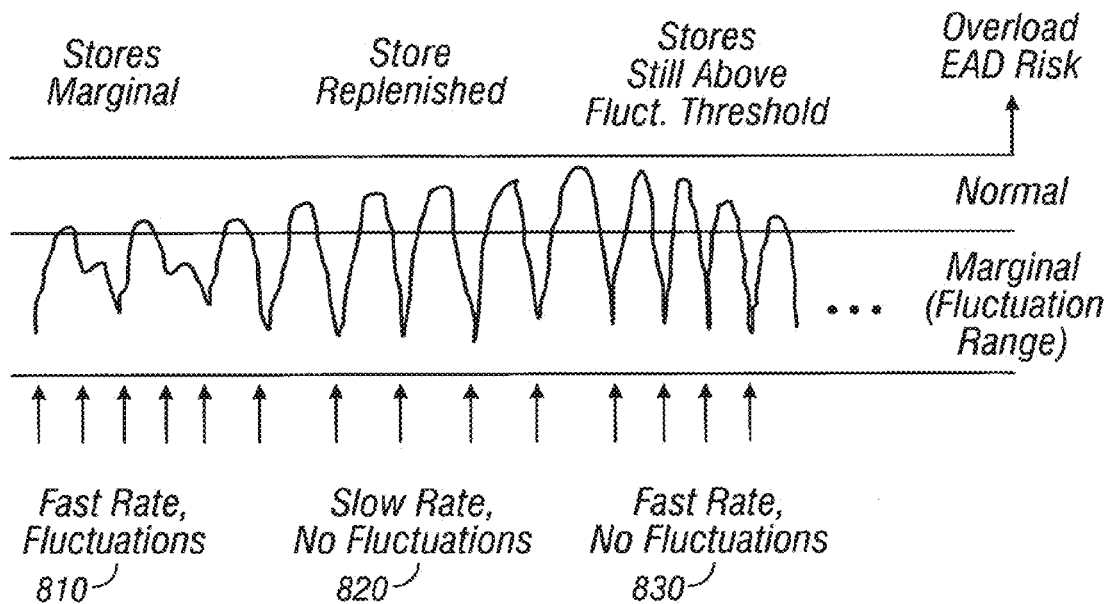
FIG. 8 illustrates one embodiment of a method of treatment of altering activation sequence to allow cellular metabolic components to regain equilibrium.
Figure 9:
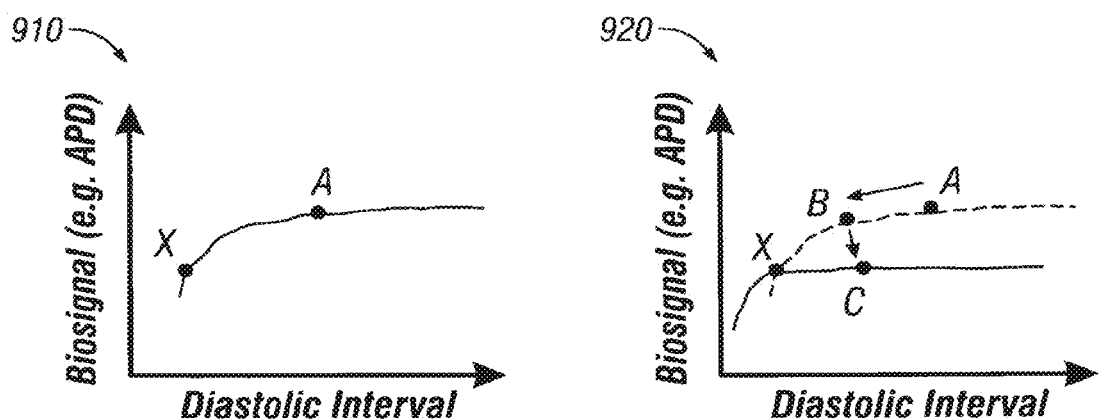
FIG. 9 illustrates embodiments of major electrical (pacing) modes of treatment.

FIG. 8 illustrates how a metabolic process may fluctuate because the rate is too fast to allow equilibrium to develop. Using concepts described with respect to FIG. 8, embodiments of methods of providing therapy to patients are described. In some embodiments, the metabolic process may be uptake of calcium content into the sarcoplasmic reticulum of a heart cell. Treatment begins by slowing the heart rate to allow the metabolic process (such as calcium) to replenish its stores. Faster activations can then be delivered to approximate the desired average heart rate, but for a short time to prevent re-emergence of oscillations. The process can then be repeated.

The graph in FIG. 8 shows the dynamics of an example of an intracellular process. The cellular process shown in FIG. 8 is regulation of calcium content in the sarcoplasmic reticulum (SR) of a heart cell. During a normal heart beat, calcium is released from the SR and then pumped back into the SR. As labeled, SR calcium content should remain between the 2 top horizontal bars. Above this range, SR calcium overload may cause early after depolarizations (EADs), which may trigger beats and cause arrhythmias. Below this range, low SR calcium may create fluctuations (with periodicities ranging from every-other-beat to every third beat or other) and also cause arrhythmias.

At the left of the graph (label 810), rapid rate pacing (narrow spacing between arrows) has depleted SR calcium so that SR calcium fluctuations are seen. In certain embodiments, therapy may now be initiated. This may assist in replenishing SR calcium, and thereby prevent oscillations and the effects of cellular derangements. Interval 820 of the graph illustrates slow pacing (wider spacing between arrows), which causes SR calcium to rise rapidly to the normal range. Preferably, pacing is not too slow, as this may cause calcium overload (that is, above the top line) and initiate arrhythmias. Pacing may then be applied more rapidly as shown in interval 830 of the graph to achieve the desired heart rate. If this is continued only for a few beats, SR calcium is not depleted and fluctuations do not re-occur. The cycle may then be repeated to approximate the previous heart rate but without fluctuations in calcium FIG. 9 illustrates embodiments of major electrical (pacing) modes of treatment. These embodiments may be used to attenuate oscillations by preventing cellular oscillations. Certain embodiments may also be used to attenuate large fluctuations in response to rate (restitution) and thus attenuate signal fluctuations that indicate cardiomyopathy and propensity for rhythm disorders.

Panel 910 shows a steep APD restitution relationship, which, as described above, may be linked with arrhythmias in the atrium (AF) or in the ventricle (ventricular tachycardia or ventricular fibrillation). If a tissue has this steep APD restitution relationship, then a premature beat (labeled X) that falls where APD slope >1 can cause wavebreak and fibrillation. This is also illustrated in FIG. 2C.

In certain embodiments, pacing modes to alter biosignal rate-response (such as APD restitution) that may be used include faster or slower pacing to alter APD rate-behavior (restitution) to prevent beat X from initiating fibrillation. For example, in panel 920, point A indicates APD of a baseline beat. Pacing at a slightly faster rate is applied to move point A to point B, with a slightly shorter APD. However, continued pacing at this faster rate moves the heart onto a different rate-behavior (restitution) curve, that is lower and left-shifted (e.g. APD shortens, and the slope is steep only for very short diastolic intervals). In panel 920, this is indicated by shifting from point B to point C. Now, the same premature beat X no longer falls on the steep portion of the rate-behavior (restitution) curve, and is less likely to induce wavebreak and fibrillation (Weiss, Karma et al. 2006). Conversely, in some individuals (particularly with more severe; cardiomyopathy), slower activation rates may flatten the rate-response (restitution) curve. Accordingly, certain embodiments allow this abnormality to be tracked so that therapy and heart rate can be tailored accordingly.

In certain embodiments, some drug treatments may be used to flatten or steepen APD restitution, and thus alter the risk for action potential fluctuations. For instance, administration of an agent to mimic adrenaline (e.g. isoproterenol) may result in similar steepening of APD restitution as discussed above, which is likely due to calcium accumulation in heart cells. Other drug treatments may be beneficial, such as beta-receptor-antagonists. In some embodiments, pacing stimulation of autonomic nerves may be performed. Such nerves lie in the inferior vena cava, superior vena cava and widely elsewhere within the body (Schauerte, Scherlag et al. 2000a). They may be accessible by pacing in the neck and other regions. In addition, it is possible to alter activation in these nerves by behaviors such as swallowing, activation of the gastrointestinal tract, or coughing. Further, in certain embodiments pacing in complex irregular intervals may flatten rate-behavior (restitution), as seen from a close inspection of data by Kalb et al. (Kalb, Dobrovolny et al. 2004). Beta-blockers and other drugs may also be used to flatten rate-behavior (restitution). Use of such drugs has been shown to work in dogs by Hao et al. (Hao, Christini et al. 2004), but no description of human rate-behavior (restitution) has been shown. Improving heart failure status may also make rate-behavior (restitution) curves less steep.

Notably, certain embodiments of described methods measure and indicate to the healthcare provider or the patient whether rate-response is favorably or unfavorably altered by each of these interventions. The measurements and interventions can be repeated until the desired result is achieved.

Figure 10:
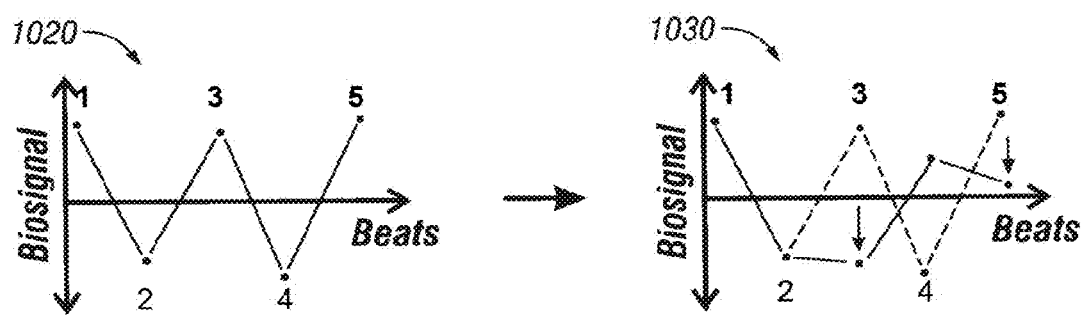
FIG. 10 illustrates out-of-phase pacing modes of treatment, to attenuate oscillations that may lead to disease.
Figure 10:
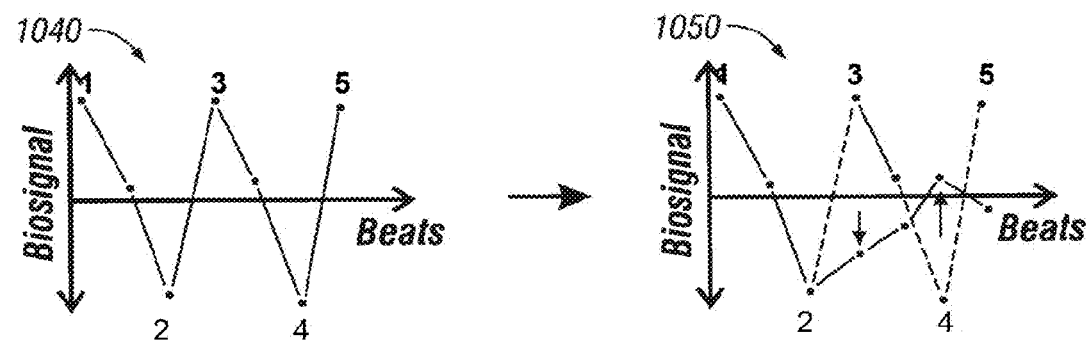

FIG. 10 depicts beat-to-beat biosignal fluctuations and therapy therefor. Panel 1020 shows fluctuations in biosignals (e.g., APD, unipolar electrogram activation-recovery-intervals) on consecutive beats. In this example, these fluctuations occur every-other beat ("alternans"), although it should be noted that the same principles apply to other beat oscillations (e.g., every 3$^{rd}$ beat or every 4$^{th}$ beat). Certain embodiments may disrupt this fluctuation by pacing out-of-phase to the initial fluctuations (arrows). That is, if the original fluctuation is long-short, then short-long pacing may be applied. In certain embodiments, the optimal strategy often does not need to pace every beat. For example, in panel 1030, pacing beat 3 shortens the biosignal (e.g., APD), and the oscillation has already broken down by beat 4. Pacing on beat 5 again prevents lengthening of the biosignal.

Panel 1040 illustrates biosignal oscillations every 3$^{rd}$ beat, but applies to any odd-beat oscillations. Panel 1050 shows the effect of out-of-phase pacing (arrows) that disrupts the original fluctuating pattern. Pacing is generally applied to stimulate the heart before the next natural beat is anticipated. This enables pacing to control the pattern and rate of the heart rhythm. The timing of the next paced beat is computed from the biosignal restitution curves (see above), to prevent further oscillations and disrupt present oscillations (examples given in FIGS. 8 and 9).

In addition to therapy with pacing strategies, therapy by altering structure or function can be performed. This may involve ablation of tissue at sites where rate-response is steep, at sites where signal fluctuations arise, or sites where nerves may influence cardiac function.

Figure 11:
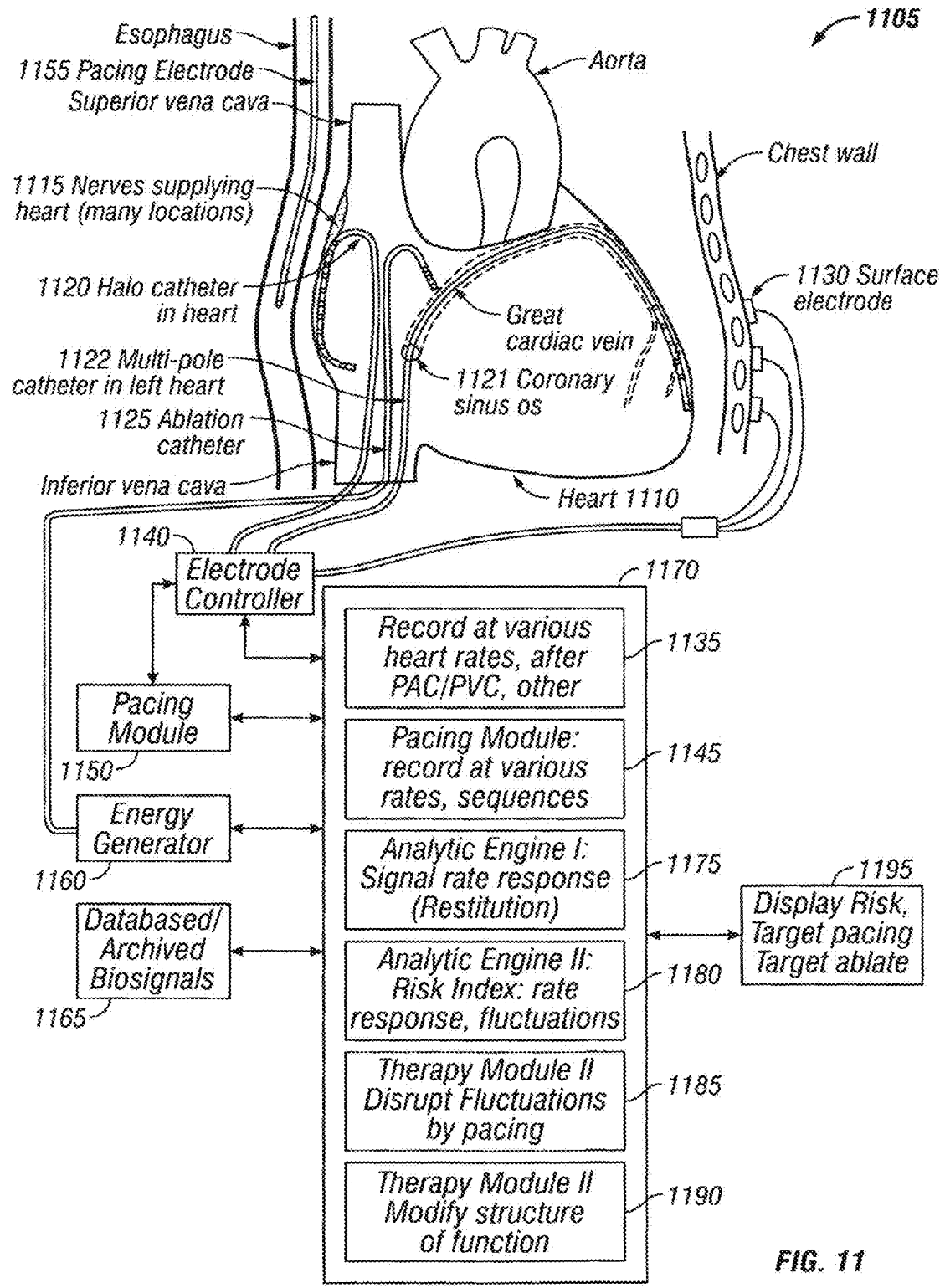
FIG. 11 illustrates one embodiment of a system for analyzing and treating heart instability.
Figure 12A:
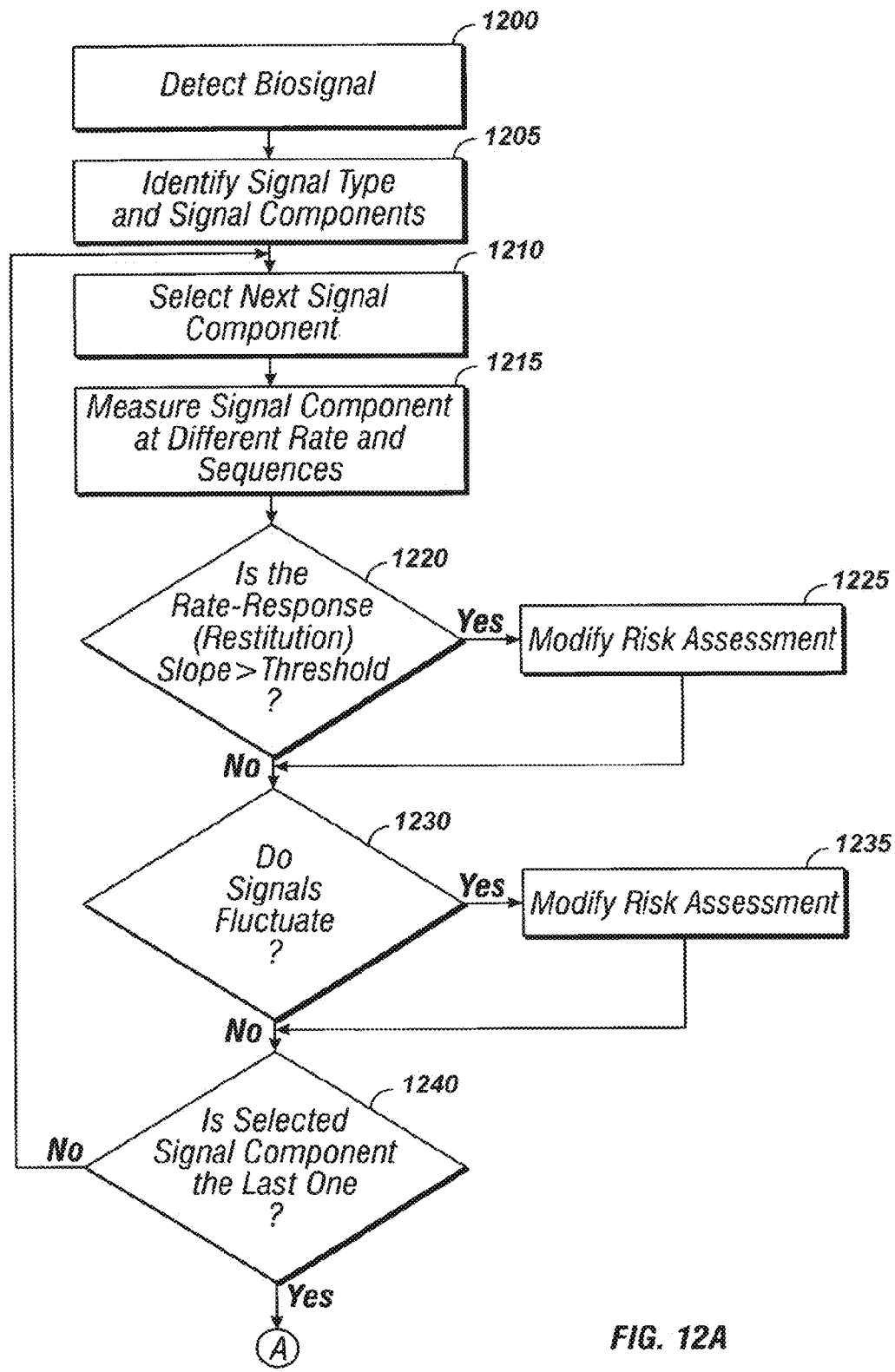
FIGS. 12A and 12B are a flowchart of one embodiment of a method of determining a risk level of a patient for developing heart instability and determining efficacy of applied treatment protocols.
Figure 12B:
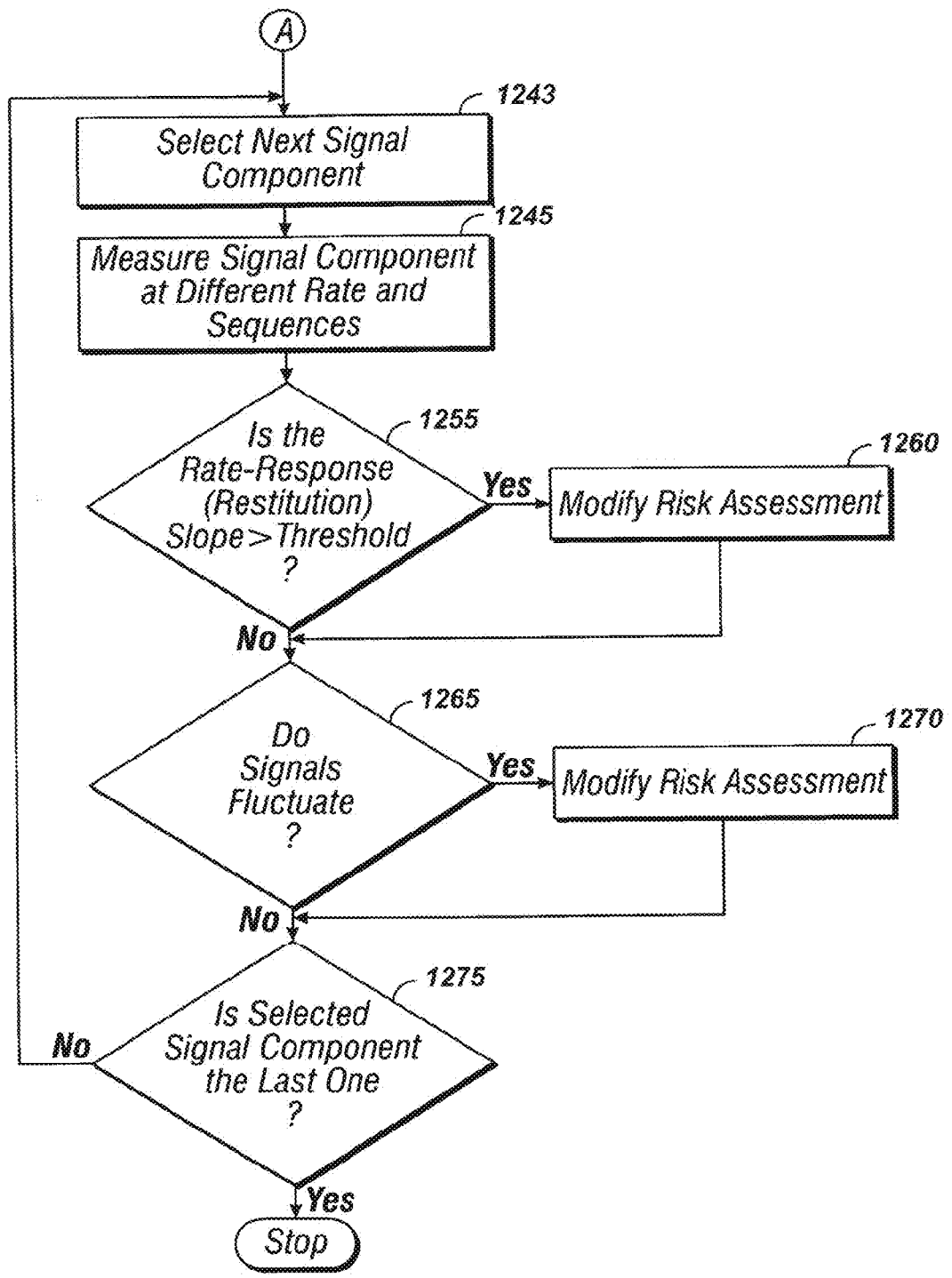

FIGS. 11, 12A and 12B illustrate embodiments of a system and method for analyzing biopotentials to develop a disease index and provide appropriate therapy in humans. In certain embodiments, the disease index can be calculated continuously during the day, or at specific times, including after treatment. FIGS. 11, 12A and 12B illustrate a variety of system components and method steps for convenience of discussion and explanation. It will be appreciated that embodiments of the invention need not incorporate all of the components or steps described with reference to these figures. Fundamentally, the various components and steps of the systems and methods described below can be used implement the sensing, analysis, and treatment modalities described above in a clinical or research setting.

Referring first to FIG. 11, in some embodiments of system 1105, electrical events in the heart 1110 are recorded with a combination of sensing electrodes. These electrodes may be electrode catheters 1120 placed within the chambers or vasculature of the heart. The electrodes may include leads from an implanted pacemaker or cardioverter-defibrillator, which may be placed via the superior vena cava or coronary sinus 1121. Electrodes can be located in proximity to the nerves 1115 supplying the heart, which are also located in the left atrium and ventricles (Scherlag, Nakagawa et al. 2005). In some embodiments of system 1105 electrodes can also be virtual (computed) electrodes from a computerized mapping system, ECG electrodes 1130, and/or stored electrograms of any database 1165. In certain embodiments an ablation catheter 1125 placed within the heart or its vasculature can be used to modify/destroy regions where signals indicate a high disease index. The ablation catheter 1125 may interface with an ablation energy generator 1160. The other electrodes may interface with an electrode controller 1140 and a pacing module 1150, all of which may communicate with a process controller 1170. Ablation or pacing electrodes can be directed to the locations of nerves 1115 supplying the heart.

The process controller 1170 may comprise various modules. These modules may include a sampling module 1135 to record the signal at various heart rates and a pacing module 1145 to provide additional heart rates for sampling the biosignal. As shown, Module 1175 is part I of an Analytic Engine and may compute a disease index based on the change of the biosignal with rate. Module 1180 is part II of the Analytic Engine and may measure the rate-response of the biometric signal and determines whether it is fluctuating. Module 1185 is the therapy module I and may interface with the pacing module to deliver therapy to disrupt biosignal fluctuations. Module 1190 is the therapy module II and may interface with an energy generator to modify structure via ablation (destruction) of tissue at sites where rate-response is steep, at sites where signal fluctuations arise, or sites where nerves 1115 may influence cardiac function. Module 1195 may comprise a display device and may provide an interactive display of the progress of the computation. The output of the system may be shown on module 1195 and may include an assessment of cardiac health (no fluctuations and absence of large signal variations with rate) or risk (the opposite). The output may also indicate ideal modes of pacing therapy and of potential ablation therapy. The modules may be multifunctional; for example, the process controller may also sample signals from other sources, such as cardiac motion from tissue Doppler imaging.

Some embodiments of system 1105 include an optimal sequence of actions and modes to provide complete and efficient diagnosis and therapy in a semi-automated fashion. These embodiments may include one or more functional modes:

1. Sampling the biosignal;
2. Analytic Engine I: determining risk score from the rate-response relationship of biosignal components;
3. Analytic Engine II: determining risk score from fluctuations in biosignal components;
4. Therapy module I: disrupt fluctuations by pacing; and
5. Therapy module II: disrupt abnormal biosignal rate-response or fluctuations by tissue modification (e.g. ablation).

In certain embodiments of uses of system 1105 involving the heart, the signal sampling mode uses one or more of ECG electrodes 1130 connected to the body surface, electrode catheters 1120, 1122 in the heart 1110, an electrode 1155 in the esophagus, and/or virtual (computed) electrograms from a mapping system. In certain embodiments these electrodes remain stationary relative to the heart while sampling the cardiac event under investigation. In an alternative embodiment, signals can be sampled retrospectively by uploading previously-stored electrograms from the database 1165 to the processor controller 1170. Alternatively, signals can be reconstructed from cardiac motion (such as tissue Doppler imaging), respiratory motion (such as on a respirator in the intensive care unit), measured pulse oximetry, and/or other biometric signals.

In certain embodiments, the process controller 1170 directs the pacing module 1150 to stimulate the heart using electrodes via 1120, 1121, 1122, 1125 in the heart 1110, electrodes 1130 on the body surface, and/or electrodes elsewhere such as in the esophagus (electrode 1155). The electrode controller 1140 may receive signals from the electrodes before, during and after pacing, and uses this information to increase the range of heart rates available for signal sampling.

Some embodiments of system 1105 monitor that adequate contact is maintained between the electrodes and the relevant tissue. For example, contact is monitored as a physician moves an electrode catheter or rotates, curves, or straightens the catheter in a region of the heart. In certain embodiments the degree of contact can be monitored by the process controller 1170 in various ways. For example, the process controller 1170 can ascertain contact by measuring variations in the amplitude of sensed signals. In another embodiment, the process controller 1170 can control the pacing module 1150 to emit pacing signals through other electrodes, and use the amplitude of detected pacing signals to ascertain contact. In yet another embodiment, the processing module 1170 can also determine contact by measuring tissue impedance.

The wider the range of rates, at which each signal is sampled, particularly at faster rates, the more accurately the rate-behavior curve may be constructed for each signal by the Analytic Engine I. By way of example, if the signal is ventricular it is first measured at resting rates (typically 60-80 beats/min) Certain embodiments implemented in an ambulatory device, may continue storing data to record at rates >100 beats/min (such as exercise and stress) and <60 beats/min (such as rest and sleep). Such behaviors may exacerbate rhythm disorders such as AF in some patients. If pacing/stimulating the heart is an option, some embodiments of system 1105 may increase heart rate by pacing to further expand the range of rates over which the biosignal is measured. Different pacing sequences may also be examined As described below, certain embodiments of system 1105 may empirically determine the activation sequence needed to eliminate fluctuations. Accordingly, therapy can be tailored to an individual person's rate dynamics.

In the ventricle certain embodiments of system 1105 may be used to:

1. detect fluctuations in electrical signals;
2. detect fluctuations in mechanical signals (from echocardiography, magnetic resonance imaging, non-contact mapping or another modality);
3. compute rate-behavior of signal components, and detect a steep relationship (marked variation in response to rate) or a shallow relationship (minimal variation in response to rate);
4. quantify conductions within regions of the heart, and detect conduction slowing for early or late beats;
5. quantify preserved or attenuated sympathovagal activation; and/or
6. compute an index of metabolic balance ("health") from said signal fluctuations in living patients.

The concept that fluctuations in clinically detectable variables indicate lack of equilibrium in cellular mechanisms for disease is novel. For instance, mechanical fluctuations (on echocardiography or blood pressure) indicate that calcium homeostasis may be unable to reach equilibrium under current conditions. This may involve cytosolic calcium, sarcoplasmic reticulum calcium, release/reuptake dynamics or inter-related systems. Electrical fluctuations in the action potential amplitude (or a surrogate) may also indicate dysregulation of calcium, of late sodium inactivation, or of transient outward current. Electrical fluctuations in action potential duration may indicate dysregulation of potassium or mechanisms related to calcium. Several other fluctuations may be detected, and this list is not intended to be exhaustive.

Fluctuations in the action potential amplitude may occur at slow rates, likely indicating calcium oscillations, which may predict ventricular arrhythmias and occur in patients with abnormalities of heart pump function. Fluctuations in the rate and shape of the action potentials may thus indicate a wide variety of cellular abnormalities. Therapy can thus be tailored to an individual's heart signal fluctuations and calibrated to the disease process and other co-morbidities in that person. Certain embodiments may track whether these and other therapies (for example, biventricular pacing) attenuate these markers.

In the atrium, certain embodiments of system 1105 may be used to:

1. detect fluctuations in electrical signals;
2. detect fluctuations in mechanical signals (e.g., from echocardiography, non-contact mapping or another modality);
3. compute rate-behavior of signal components, and detect a steep relationship (marked variation in response to rate) or a shallow relationship (minimal variation in response to rate);
4. quantify conduction within regions of the heart, and detect conduction slowing for early or late beats;
5. quantify preserved or attenuated sympathovagal activation, including signal components reflecting ganglionic plexus innervation of the atria;
6. compute an index of metabolic balance ("health") from said signal fluctuations in living patients.

Again, the concept that fluctuations in a clinical variable can indicate lack of equilibrium in cellular mechanisms is novel. As in the ventricle, fluctuations in atrial action potential amplitude may occur at slow rates, again suggesting calcium oscillations, which may predict AF. These fluctuations are more likely to occur in patients with atrial abnormalities, and may represent an important component of the AF substrate. Fluctuations in the rate and shape of the action potentials may thus indicate a wide variety of cellular abnormalities. Therapy can thus be tailored to an individual's heart signal fluctuations and calibrated to the disease process and other co-morbidities. Certain embodiment may thus track whether these or other therapies (for example, ablation, certain drugs) attenuate these markers.

As discussed, certain embodiments of system 1105 can thus detect potentially detrimental effects of other treatments or activities. For example, right ventricular pacing may reduce left ventricular systolic function (David 2002). However, it is difficult to predict individuals who will suffer this effect. Certain embodiments of system 1105 can identify such patients from fluctuations in human biosignals (action potentials, unipolar or bipolar electrograms from a device lead, or T-wave from the ECG). Autonomic innervation may also be tracked through its effects on APD rate-behavior. Thus, sympathovagal stimulation that favors AF may make APD rate-behavior steeper, which may be tracked in certain embodiments. Worsening heart failure may lead to calcium overload and other failed regulatory systems, causing signal fluctuations that may be detected in certain embodiments. Pro-arrhythmia from anti-arrhythmic and other medications (e.g. erythromycin) may be detected in certain embodiments. Ischemia, both subclinical and clinically evident, may be detectable using ventricular signal fluctuations in certain embodiments. Inotropic therapy with dobutamine or milrinone can produce arrhythmias This may be mediated by cellular changes that can be tracked in certain embodiments.

Certain embodiments of system 1105 can also detect potential therapeutic benefits. For example, biventricular pacing may improve heart failure (Bristow, Saxon et al. 2004). An early sign of improvement is reduced biosignal fluctuations, such as electrical indices of action potentials (electrograms from implanted devices, or monophasic action potentials) reflecting calcium overload, which may be tracked in certain embodiments.

Further, autonomic effects can be tracked through effects on APD rate-behavior (restitution). Improved sympathovagal 'balance' that protects against atrial and ventricular arrhythmias may attenuate rate-response (making restitution more shallow), that can be tracked in certain embodiments. In addition, Beta-blocker and other neurohormonal therapy may produce less marked rate behavior of electrical signals (restitution) and attenuate biosignal fluctuations which may be traced in certain embodiments.

FIGS. 12A and 12B illustrate an embodiment of a method of determining a risk level of a patient for developing heart instability using certain embodiments of system 1105. In certain embodiments, the method of FIGS. 12A and 12B analyze electrical events in the heart via electrodes described with reference to FIGS. 1A-1C. In FIG. 12A, at step 1200, a biosignal may be detected at the electrodes described with reference to FIGS. 1A-1C.

This signal could come from a wide variety of sources. In one embodiment, at a step 1205 the signal type of the detected biosignal may be identified from a lookup table for a multi-input system. In other embodiments the user may manually input the signal type being monitored/analyzed. The signal type identification also determines if the signal arises from the heart, brain, respiratory system, gastrointestinal tract, urogenital system, or some other source. If heart-related, the signal can be identified as a surface ECG, intracardiac, echocardiographic or other. If intracardiac, the signal can be identified as an action potential (monophasic action potential or approximated signal derived from contact pressure from a bipolar electrode with wide bandpass filtering), bipolar electrogram, unipolar electrogram, or some other appropriate signal type. The lookup table may also indicate that the identified biosignal is of a signal type made up of one or more components. In certain embodiments, the lookup table can be a comprehensive biosignal inventory, with data on the distinct components of each biosignal type and the physiological significance of each component. Each component of a biosignal may vary independently with rate and may fluctuate between beats. Each signal component may reflect a distinct aspect of normal or abnormal physiology and thus reflect "high risk". Below are examples of signal types and components that may be included in the lookup table. However, the lookup table is not limited to the examples below and may include signal types and components for other heart-related signals, signals involving other muscles (e.g. skeletal muscle, bladder and gastrointestinal tract), signal involving the brain, and/or signals involving the nervous system.

The signal may be an ECG with atrial components (P-wave, PR interval) and ventricular components (QRST waves). In certain embodiments described herein, for the atrium, it may be determined how P-wave duration varies with rate as a measure of atrial conduction slowing. For the ventricle it may be determined how the QT interval varies with rate as a measure of ventricular APD rate-behavior (restitution).

As described in detail above, the signal may be human action potentials in the atrium and/or ventricle. The signals may be unipolar electrograms from the human atrium and ventricle. Indeed, such signals convey many of the same information as the monophasic action potential. Moreover, with sufficient contact pressure and wide filter settings (for instance, 0.01 to 500 Hz), a traditional electrode can record a signal very similar to a monophasic action potentials. The signals may also be traditional bipolar electrograms from the human atrium and ventricle. Certain embodiments of system 5 may determine rate response and fluctuations in each component.

Other signals that can be handled by certain embodiments of system 5 include electrical signals indicating brain wave activity, respiratory activity, and gastrointestinal activity, and signals measured from autonomic ganglia as sympathetic nerve activity.

Between steps 1210 and 1240, the components of the signal may be parsed (processed stepwise). For a monophasic action potential (MAP), the parsed components may include phase 0 (upstroke), phase I, phase II, phase III and phase IV. For an ECG, the parsed components may include the PR, QRS, QTU, ST, JT and JTU intervals. For example, the ECG signal may be separated into atrial components (the P wave and PR interval), ventricular depolarization (the QRS complex), and ventricular repolarization (the T wave). QRS complexes can be identified using methods discussed by Watanabe et al. (Watanabe, Bhargava et al. 1980) and U.S. Pat. Nos. 4,552,154 issued to Hartlaub, and 6,035,231 issued to Sommo Individual QRS complexes are then aligned using one of several columnar techniques. Examples include methods that align electrograms about the point of largest positive or negative slope, methods that align electrograms about their peak values, methods that minimize the mean square differences of the electrograms, and methods based on metrics based on derived signals. T-waves may also be identified and aligned similarly. Atrial activity may be considered to lie in the intervening intervals.

If the signal is an action potential (FIG. 1), phases 0, 1, 2 and 3 may be separated. Components of interest of an action potential include depolarization (phase 0), repolarization (phases 1-3), phase II amplitude and action potential duration (time interval from phase 0 to phase 3). If the signal is a unipolar electrogram, it may be segregated into depolarization and repolarization phases. Each may be analyzed for the waveform shape as well as duration. If the signal is a bipolar electrogram, it may be segregated into depolarization and repolarization phases. Each may be analyzed for the waveform shape as well as duration.

At step 1210, the next signal component of the signal is selected. Continuing at step 1215 the rate response of the selected component is measured at one or more rates and using one or more pacing sequences. Rate response may be determined for a wide range of observed heart rates. If available, pacing may also be used to increase the heart rate to provide a wider range of rates at which the component signal response is measured to comprehensively assess rate response.

Certain embodiments may also use an adaptive series of programmed sequences to attenuate fluctuations. Such sequences may include a series of slow then fast beats tailored to the specific non-linear processes under consideration. For example, suppose a heart rate of 100 beats/min is desired (cycle length 600 ms), but fluctuations arise above 90 beats/min (cycle length shorter than 667 ms), suggesting derangements in calcium homeostasis. A sequence of 700 ms-700 ms-700 ms-700 ms-400 ms-400 ms provides the desired average rate, but the first 4 beats should prevent fluctuations (by allowing replenishment of cellular calcium stores). If stores are sufficiently replenished, the next two fast cycles (#5-#6) now may not give risk to fluctuations. The sequence can then repeat. A variety of such sequences may be tested in step 1215, calibrated to whether fluctuations arise or are attenuated. These tests may then be used to tailor therapy in later stages of certain embodiments of the described method.

At step 1220 the rate-response ("restitution") curve may be constructed for the selected component. Depending on the type of signal component, different calculations may be done to construct the restitution curve. Variations in monophasic action potential duration (time from phase 0 to the phase III terminus) with rate may be calculated at step 1220. This is known as APD restitution (Franz, Swerdlow et al. 1988a). Restitution for additional components may also be calculated. For instance, the rate response (restitution) for phase 0 upstroke velocity may be calculated as it is a measure of sodium channel fluctuations with rate (and resting membrane potential), which may influence conduction slowing. Rate response of the amplitude of phase II of the action potential (or of a unipolar electrogram) may be calculated as it is a surrogate index of calcium, as mentioned above. If at step 1220 it is determined the slope of the calculated restitution curve is greater than a threshold value, the process continues to a step 1225 where a risk score is incremented. For example, at step 1225 high risk may be assigned based on predefined properties of the biosignal rate-behavior (restitution) and the signal type. For monophasic action potential duration (MAPD), risk may be ranked higher at step 1225 if it is determined the rate-behavior (restitution) maximum slope >1 at step 1220 (Weiss, Karma et al. 2006). The risk score is described with greater detail below. The process then continues to step 1230. If at step 1220 it is determined that the slope of the restitution curve is not greater than the threshold value, the process proceeds to step 1230.

At step 1230, it is determined whether the signal component fluctuates. For example, the biosignal may fluctuate at a native (baseline) heart rate. If it is determined the signal fluctuates, the process proceeds to step 1235, where the risk score is incremented. For example, at step 1235 a risk score of "Imminent risk" may be assigned if the biosignal fluctuates at native (baseline) heart rate. High risk may also be assigned at step 1235 if the signal fluctuates at the current heart rate. The process may then continue to step 1240. If at step 1230 it is determined the signal does not fluctuate, the process continues to step 1240. At step 1240, it is determined if the selected signal component is the last signal component of the biosignal (i.e., all the signal components have been measured). If it is determined the selected component is not the last signal component, the process returns to step 1210 where a signal component that has not previously been selected is selected to be measured. If it is determined the signal component is the last signal component, the process proceeds to step 1243 as illustrated in FIG. 12B.

Steps 1243 to 1275 may track cardiac status during therapy by measuring each component of the biosignal. Signal analysis and risk assignment may be performed before intervention at steps 1210-1240, and may be repeated after an intervention at steps 1243-1275. As before, each signal component may be processed for rate response.

At step 1243, a signal component of the biosignal is selected to be measured. Continuing at step 1245, biosignal variations may be assessed for all heart rates observed and, if available, by pacing at faster heart rates and at various sequences as described above. The effect of the intervention may then be determined Further, at step 1255 it is determined if rate response (restitution) is steeper than it was before the intervention. If it is determined that the slope is greater than before intervention, the process may proceed to a step 1260, where the risk score is flagged as "increased risk" and/or the intervention is flagged as "detrimental intervention. The process then proceeds to step 1265. If at step 1255 it is determined the restitution is not steeper than previously measured, the intervention may not be detrimental and the process proceeds to step 1265.

At step 1265 it is determined if the biosignal fluctuates more than before treatment or fluctuates when previously it did not. If at step 1265 it is determined that the signal fluctuation has increased, the process proceeds to a step 1270 where the risk score is flagged as "increased risk" and/or the intervention is flagged as "detrimental intervention." The process then proceeds to step 1275. If at step 1265 it is determined the signal fluctuation has not increased, the intervention may not be detrimental and the process proceeds to step 1275. At step 1275 it is determined if the selected signal component is the last signal component of the biosignal (i.e., all the signal components have been measured). If it is determined the selected component is not the last signal component, the process returns to step 1243 where a signal component that has not previously been selected is selected to be measured. If it is determined the signal component is the last signal component, the process ends.

In some embodiments, ECG and electrogram data may be uploaded from a database 160 for analysis in an analogous fashion to the described real-time mode of operation. Data from the database can be from the same or different patients, recorded at any time and using any acquisition system.

Analytic Engine I 1175 in certain embodiments may be implemented in software. Certain embodiments of Analytic Engine I 1175 operate quickly and are suitable for real-time as well as off-line analysis.

In certain embodiments, steps 1220-1225 of the process of FIG. 12A may be carried out by Analytic Engine I 1175. For example, Analytic Engine I 1175 may determine the rate-response (restitution) of each component.

Certain embodiments of the risk scoring system may be based on APD rate-behavior (restitution), alternans, and/or conduction rate-behavior (restitution) (Analytic Engine I). Certain embodiments of system 1105 may initially use a "default" mode of risk scoring. Some of these embodiments may also have an adaptive design that may tailor both risk assignment and therapy to observed fluctuations and rate response in the individual.

In certain embodiments of system 1105, steps 1230-1235 may be carried out by the Analytic Engine II 1180. Analytic Engine II 1180 may determine whether biosignals or their components fluctuate.

Elimination of signal fluctuations using certain embodiments of system 1105 may prevent AF onset. It has been found in some cases that rapid atrial pacing did not cause AF. Notably, in some of these cases, conduction slowing arose near the pacing site at very fast rates. Patients with less significant disease may show conduction slowing only at very fast rates, while more significant disease may produce more complex effects. In some cases, signal fluctuations are present (at slow rates), yet are attenuated by conduction slowing, which causes local capture block and thus prevents AF.

As discussed above, signal fluctuations indicate disease risk. Fluctuations at fast rates may occur in persons with low/intermediate risk (and minimal/intermediate cellular or structural disease). Conversely, fluctuations at slow rates may be seen in patients with substantial disease and greater substrate. The data presented shows this for the ventricle and atrium.

Embodiments of methods that may be performed using embodiments of system 1105 include pacing methods to modulate the shape of the rate-behavior (restitution) curve of electrical signals, or to disrupt fluctuations in the biosignal, and thus normalize abnormal calcium handling and prevent progression of contractile dysfunction and/or arrhythmia.

In certain embodiments; the process controller 1170 controls the pacing module 1150, to stimulate the heart using electrodes 1120, 1122 in the heart, electrodes 1130 on the body surface, and/or electrodes elsewhere such as from the esophagus (electrodes 1155). The electrode controller 1140 receives signals from the electrodes before, during and after pacing. Pacing may be used to increase heart rate and introduce extra beats to alter biosignal rate-response and disrupt biosignal fluctuations.

Pacing can be applied via any electrode. In certain embodiments, pacing may be applied via implanted electrodes of a pacemaker or implanted cardioverter-defibrillator in the outpatient setting, or from an ablation catheter 1125 at electrophysiology studies. Pacing techniques including burst pacing and multiple extra stimuli can be used. The pacing stimulus may be monophasic, biphasic, or triphasic.

Certain embodiments of system 1105 use pacing to modify the rate-response (i.e. restitution) of the biosignal or to disrupt the pattern of biosignal fluctuations. Flattening of rate-behavior (restitution) or attenuation of fluctuations may reduce the propensity to arrhythmias.

Certain embodiments of system 1105 may utilize an adaptive pace sequence approach to eliminate signal fluctuations. Sequences may be tailored to the individual patient, and may be modified at different times. By monitoring electrical signal fluctuations in real-time, certain embodiments of system 1105 can iteratively solve for the optimum pace sequence. Iterations can commence from basic "defaults" for each patient, established as part of Analytic Engine II 1180.

Other cellular derangements can be addressed by tailored pacing in this fashion, titrated to the relevant component of electrical fluctuations. Such pacing may prevent the sequelae from cellular derangements, including the onset of heart rhythm disorders and progression of cardiomyopathy.

From a cell mechanism point of view, the methods that may be implemented by system 1105 may be viewed as follows:

A. Design/quantify cycle periodicity
   a. If varying on an even beat basis (every fourth or second beat)—intervene on odd beats;
   b. If varying on an odd beat basis (every third or fifth beat)—intervene on even beats;

B. Determine Individualized Rate thresholds for different Cellular Processes (e.g. heart) by progressively increasing rate until:
   a. AP Phase I oscillations occur signaling incomplete recovery of $I_{Na}$;
   b. AP Phase II oscillations occur signaling abnormal calcium handling, potentially abnormal Ito kinetics, and/or abnormal late sodium inactivation kinetics;
   c. AP Phase III oscillations occur, which involves potassium currents, such as $I_K$, and is often dependent upon the APD restitution. This operates at fast rates.

C. Calibrate against disease based on the measurable effects of ion channels
   a. In other tissues, such as the brain, the measurable effects of other ion channels can be calibrated against disease. For instance, variations in $I_{Na}$, $I_K$ can be measured and modeled against observed epileptiform activity.
   b. In the atrium, P-P intervals may be varied to ameliorate calcium overload on some cycles to reduce AP shape variations.
   c. In the ventricle, the R-R intervals may be varied to ameliorate calcium overload on some cycles to reduce AP shape variations. PR intervals may also be varied, thus varying R-R intervals to ameliorate cellular metabolic dynamics and AP shape variations. This variation may support the beneficial effect of certain irregular rhythms (e.g., bigeminy or trigeminy) which are not pro-arrhythmic in atrium or ventricle.

Certain embodiments of system 1105 may use a clinical measure to indicate cellular health. In one embodiment, calcium fluctuations that indicate a cellular manifestation of cardiomyopathy are determined As shown above, fluctuations in the action potential shape (particularly phase II) may indicate oscillations in cellular calcium. Such oscillations, in turn, may occur after calcium overload as described in cardiomyopathy. Thus, certain embodiments of system 1105 may provide a clinical index that probes cardiomyopathy from oscillations in cardiac signals (particularly phase II of action potentials).

Certain embodiments of system 1105 may indicate to the healthcare provider or patient whether fluctuations are favorably or unfavorably altered by interventions. This may be repeated until the fluctuations are attenuated or abolished.

Certain embodiments of system 1105 are also designed to stimulate cardiac nerves to modulate their impact on heart functioning. For instance, it is known that elevated sympathovagal balance can precipitate AF in animals (Patterson, Po et al. 2005). System 1105 may perform electrical or other energy source stimulation of the atrium or ventricle to alter the biosignal rate-behavior or the presence of biosignal fluctuations.

In some embodiments, Therapy Module II 1185 may operate during invasive electrophysiology studies, and may modify tissue structure where the biosignal rate-response is steep, or where biosignal fluctuations occur. This may be achieved by ablating tissue, by altering it via heating or cooling, and/or by using electromagnetic fields.

In certain embodiments, the energy generator 1160 may be activated to apply energy (radiofrequency, infrared, cryoablation, microwave radiation, or other energy) via the ablation electrode 1125. The electrode 1125 can be moved within the heart manually by an operator, or remotely using robotic or computer assisted guidance. In certain embodiments, Therapy Module II 1185 may only be actuated after pacing interventions have failed to attenuate the steepness of rate-behavior (restitution).

In certain embodiments, after ablation, system 1105 remotely moves the catheter 1125, or prompts the user to move the catheter 1125, to an adjacent location to assess its rate response. If rate-behavior (restitution) is steep, or fluctuations are observed, ablation may be repeated. This may result in elimination of tissue where steep rate-behavior (restitution) or fluctuations are observed (both indicating diseased tissue and/or cardiomyopathy, see FIGS. 2A-4). In the certain embodiments, system 1105 can engage remote catheter navigation to survey the entire atrium for such fluctuations.

Certain embodiments of system 1105 may also be designed to ablate cardiac nerves to modulate their impact on heart functioning. Accordingly, certain embodiments of system 1105 may use radiofrequency or other energy source to alter the biosignal rate-behavior or the presence of biosignal fluctuations.

Permanent tissue modification may not be necessary in some circumstances. Accordingly, in certain embodiments, subthreshold pacing may be applied, or an electromagnetic field may be used to modulate tissue function for a desired period of time. The type of treatment used may be modulated in real-time depending upon risk assessment (from signal restitution and fluctuations).

The above described approach of introducing "planned" rhythm irregularities is novel and appealing. Although such irregularities may appear potentially detrimental, it should be noted that many naturally observed "regular irregularities" are benign (i.e., not dangerous), such as atrial or ventricular bigeminy (where every-other-beat is faster and/or from a different source) and normal fluctuations in heart rate ("sinus arrhythmia"). Similarly, slow rates are central to beta-blocker therapy, which is widely accepted to improve health at body, organ, and cellular levels.

Certain embodiments also predict which individuals will develop AF and deliver therapy that carefully modulates atrial function to reduce these fluctuations and prevent the development of AF.

The embodiments above described in relation to heart-related electrical signals. However, one of ordinary skill in the art will recognize that similar embodiments may be used for analyzing other electrical signals. Additional embodiments may be used for striated muscle (peripheral muscle), smooth muscle in the gastrointestinal, urogenital and respiratory systems, and in association with the electroencephalogram or invasive surgical techniques such as open heart or brain surgery.

One embodiment analyzes action potentials or surrogate signals of activation and recovery from the beating heart. These signals may be detected from an ECG, implanted pacing electrodes (in the heart or other tissues via far-field detection), an echocardiogram (that indicates activation and recovery), or other sources. In certain embodiments, pacing and ablation electrodes can be used within the beating heart and in nerves that supply the heart. Other embodiments may use signals derived from heart contraction, including reflected sound waves or electrical impedance changes. Certain embodiments may analyze signals and apply pacing to skeletal muscle in individuals with muscular diseases. Some embodiments may analyze signals and apply treatment to the gastrointestinal tract. Other embodiments may apply treatment to the muscles of the respiratory system.

Certain embodiments calculate the changes in response to rate (also known as "restitution") of electrical heart signals, and fluctuations in said signals, to calculate a risk index for abnormal rhythms such as atrial fibrillation (AF; in the top chambers, or atria) or ventricular fibrillation (VF; in the bottom chambers, or ventricles). As described below, steep slope of the rate-behavior or fluctuations may reflect "a sick heart," or other metabolic abnormalities that may indicate a predisposition to AF in the atria or VT/VF in the ventricles. Certain embodiments can use action potentials (such as monophasic action potentials or other surrogates such as electrograms from implanted atrial leads) from the human heart to construct this risk index. Some embodiments may use unipolar or bipolar electrograms and/or signals representing cardiac motion from detailed echocardiographic, CT, or magnetic resonance imaging.

If fluctuations are observed, or expected from the rate-response (restitution) curve, certain embodiments may apply therapy to disrupt the pattern of fluctuations or modify restitution. This therapy may attenuate cellular derangements in cardiomyopathy and potentially reduce the risk of arrhythmias.

Certain embodiments can thus determine if cardiac disease (cardiomyopathy) is progressing—due to native disease or as a side-effect of potentially detrimental interventions such as right ventricular pacing, or inotrope therapy (e.g. with dobutamine). Certain embodiments may use ablation to modify tissue that exhibits abnormal fluctuations. Therapy can also be applied to nerves that regulate heart function and may cause rhythm disorders. Certain embodiments can track such therapy. Certain embodiments may also track progression of cardiac disease from biventricular pacing, after ablation (for atrial fibrillation or ventricular tachycardia), beta-blocker therapy, etc.

In one embodiment, stimulation of the top chamber of the heart (atria) or bottom chamber (ventricle) can be performed. The stimulation assists in cellular regulation of the targeted deranged metabolic (or ionic) process. Accordingly, certain embodiments may attenuate heart signal oscillations that occur due to abnormal calcium homeostasis. For example, in certain embodiments, slow rate pacing may first be applied to the heart to restore sarcoplasmic reticulum calcium stores. The duration of slow pacing may be titrated carefully, to avoid calcium overload that produces extra beats (from after depolarizations) and triggers arrhythmias. After this period of relative calcium loading, a period of faster pacing may be used to achieve the desired average heart rate. Again, this may be titrated carefully to avoid calcium depletion that may again produce oscillations. The reason for this rate variation is that calcium sequestration and release kinetics are non-linear. In certain embodiments the impact of rate variations on action potential duration (via restitution) is also considered.

In other embodiments, methods of treatment are performed including increasing or reducing the activation rate, and directly disrupting the regularity of oscillation. For example, if fluctuations occur every third beat, in certain embodiments the apparatus may alter activation of the atrium or ventricle every fourth or second beat—out of phase with the native oscillation—to disrupt the fluctuations.

In some embodiments, destruction (ablation) may be targeted at tissue responsible for fluctuations or abnormal rate-behavior (which leads to fluctuations) of biological signals. Ablation may include, but is not limited to, conventional sources (radiofrequency energy, cryoablation), and alternative sources, including microwave, ultrasound and external beam irradiation.

In yet other embodiments, function of the tissue responsible for the heart signal fluctuations may be altered using external electromagnetic fields, pacing at a subthreshold intensity, and/or other interventions.

Atrial cardiomyopathy (heart failure of the top chamber of the heart) may be detected and tracked in certain embodiments. Certain embodiments detect signatures of atrial cardiomyopathy. Certain embodiments may provide methods for attenuating derangements in the intracellular handling of calcium and other ions due to cardiomyopathy. The attenuation reduces the severity of atrial cardiomyopathy (by potentially reducing contractile dysfunction) as well as "side-effects" such as heart rhythm disorders (atrial fibrillation). Certain embodiments provide a method for tracking atrial cardiomyopathy in humans. Certain embodiments described herein calculate an index, in the intact human heart, of specific abnormalities in atrial cell function ("cell health") that indicate atrial cardiomyopathy and risk for side-effects including atrial fibrillation. This index can be used to track whether these abnormalities improve or worsen with therapy. The index can also be used to analyze atrial action potentials, a surrogate signal from a catheter, signals from an implanted atrial lead (from a pacemaker or defibrillator), signals from echocardiography, and/or signals from the electrocardiogram.

Certain embodiments described herein detect specific abnormalities in atrial cell function ("cell health") that likely cause heart rhythm disorders and which may represent early forms of atrial cell disease (cardiomyopathy). These abnormalities may be present at heart rates easily found during the activities of daily living, yet become exaggerated just prior to AF. Thus, certain embodiments can be used to continuously track the propensity for AF during therapy and then deliver therapy if the propensity (signal oscillations) is observed.

Certain embodiments described herein target specific cellular abnormalities in regulation of atrial cell physiology, which may be central to weakened atrial contraction and the initiation of AF. Thus, ameliorating this disequilibrium may improve atrial cardiomyopathy as well as risk for AF and other sequelae. As a result, certain embodiments are configured to improve and reverse abnormal features of atrial cardiomyopathy and may use methods described herein to track whether the therapy is working.

Certain embodiments herein introduce a paradigm shift in assessing ventricular cardiomyopathy. Because they may assess, detect, and act upon the biochemical balance of ventricular cells, guided by homeostatic mechanisms that are very likely central both to contractile (mechanical) and heart rhythm abnormalities in human beings in real time, they can dynamically indicate cellular health and disease risk and guide therapy to normalize these abnormalities. In animal experiments, cellular calcium balance provides a precise measurement of ventricular cell function and the risk for VT/VF (Laurita and Rosenbaum 2008). Embodiments of methods are described herein that significantly improve upon existing methods for detecting risk for worsening ventricular cardiomyopathy or risk for VT/VF. These embodiments can be used to analyze ventricular action potentials, signals from a ventricular lead, signals from echocardiography or signals from the electrocardiogram.

Certain embodiments of methods may focus on oscillations in action potential shape (see below, particularly phase II). Examining action potential shape is a new field, since most or all prior art examines action potential duration. Some methods described herein may focus on fluctuations in action potential shape, which may indicate cellular imbalances (disequilibrium) in calcium and other metabolic processes, as changes in action potential duration may not be sensitive to such fluctuations. Certain embodiments of methods described herein measure slow rate oscillations and provide potential therapy.

Embodiments described herein link the risk for VT/VF with cellular abnormalities that are detectable from the beating heart in individuals. Unlike prior methods, whose association with VT/VF is indirect, certain embodiments described herein assess specific abnormalities in ventricular cell function ("cell health") caused by ventricular cardiomyopathy which explains why VT or VF initiates at a cellular level. Some such embodiments may measure these fluctuations in the action potentials of ventricular cells. Furthermore, in certain embodiments these fluctuations may be tracked to determine if therapy is effective.

Embodiments described herein may use novel pacing strategies, and other techniques, to assist the heart in normalizing cellular homeostasis (in calcium and other metabolic processes). Treatment may be tailored to each patient. Certain embodiments may be used to detect attenuation of fluctuations in action potentials (or surrogate signals) providing a method to determine if cardiac resynchronization therapy is improving heart failure at the tissue and cellular level. Similarly, certain embodiments can detect exaggerated fluctuations if heart failure is worsening (such as from right ventricular pacing). In certain embodiments, after treatment of these abnormalities, these fluctuations can be continuously tracked as a marker of cellular health.

The implementation of the systems and methods described herein is based largely upon digital signal processing techniques. However, it should be appreciated that a person of ordinary skill in this technology area can easily adapt the digital techniques for analog signal processing.

Those of skill will recognize that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal While the above detailed description has shown, described, and pointed out novel features of the invention as applied to various embodiments, it will be understood that various omissions, substitutions, and changes in the form and details of the device or process illustrated may be made by those skilled in the art without departing from the scope of the invention. As will be recognized, the invention may be embodied within a form that does not provide all of the features and benefits set forth herein, as some features may be used or practiced separately from others. The scope of the invention is indicated by the appended claims rather than by the foregoing description. All changes which come within the meaning and range of equivalency of the claims are to be embraced within their scope.

The invention claimed is:

1. An apparatus associated with diagnosis and treatment of a suspected heart rhythm disorder in a beating human heart, the apparatus comprising:
   one or more sensors configured to detect one or more signals from the beating human heart over a plurality of time segments;
   a diagnostic unit configured to calculate one or a combination of signal changes in response to a variation in at least one of rate and regularity induced in the beating human heart, the variation being induced to determine whether the signal changes indicate the suspected heart rhythm disorder, the signal changes being in at least one of signal shape, duration of signal components, signal amplitude and signal characteristics among a first time segment and a second time segment of the plurality of time segments, wherein at least a portion of the second time segment differs from at least a portion of the first time segment; and
   a therapy unit configured to modify at least one of tissue structure and function based at least in part on the signal changes determined by the diagnostic unit.

2. The apparatus of claim 1, wherein the signals represent action potentials.

3. The apparatus of claim 2, wherein the signal changes in the signal characteristics comprise a change in a slope of a rate-response associated with the signal changes calculated in response to the variation in at least one of rate and regularity induced in the beating human heart.

4. The apparatus of claim 2, further comprising a detection unit to detect conduction slowing.

5. The apparatus of claim 4, wherein the conduction slowing affects at least one of the signal changes calculated in response to the variation in at least one of rate and regularity induced in the beating human heart.

6. An apparatus to assess a risk associated with a suspected heart rhythm disorder comprising:
   at least one sensor; and
   an analytic engine comprising:
      a module configured to measure a signal received via the at least one sensor from a beating human heart;
      a module configured to calculate a change in the signal among at least a first time segment and a second time segment, the change in the signal being in response to a variation in at least one of rate and regularity induced in the beating human heart, the variation being induced to determine whether the change in the signal indicates the suspected heart rhythm disorder, wherein at least a portion of the second time segment differs from at least a portion of the first time segment; and
      a module configured to generate a risk score for the suspected heart rhythm disorder determined based at least in part on the change in the signal.

7. The apparatus of claim 6, further comprising a module configured to construct a rate-response curve and measure a slope of the rate-response curve.

8. The apparatus of claim 7, wherein fluctuations in the rate-response curve are affected by signal changes in at least one of shape of the signal, duration of components of the signal, amplitude of the signal and signal characteristics in response to the variation in at least one of rate and regularity induced in the beating human heart.

9. The apparatus of claim 6, further comprising a module configured to control excitation of tissue of the beating human heart.

10. The apparatus of claim 9, wherein excitation of tissue comprises pacing the tissue to change the rate associated with the signal.

11. The apparatus of claim 6, wherein the change in the signal is calculated between alternate beats of the beating human heart.

12. The apparatus of claim 9, wherein excitation of tissue comprises pacing the tissue out-of-phase with changes calculated in the signal at different rates.

13. The apparatus of claim 6, further comprising a module configured to control modification of tissue of the beating human heart.

14. The apparatus of claim 13, wherein modification of tissue comprises ablation of the tissue.

15. The apparatus of claim 6, further comprising:
   an energy generator coupled to an ablation electrode;
   an electrode controller coupled to the at least one sensor;
   a process controller coupled to the electrode controller and the energy generator;
   a sampling module configured to record the signal; and
   a pacing module configured to send a pacing signal to a pacing electrode, wherein the signal excites tissue.

16. An apparatus associated with treatment of a suspected heart rhythm disorder in a beating human heart, the apparatus comprising:
   one or more sensors configured to detect one or more signals from the beating human heart over a plurality of time periods;
   a diagnostic unit configured to calculate one or a combination of signal changes in response to a variation in at least one of rate and regularity induced in the beating human heart, the variation being induced to determine whether the signal changes the suspected heart rhythm disorder, the signal changes being in at least one of signal shape, duration of signal components, signal amplitude and signal characteristics among a first time period and a second time period of the plurality of time periods, wherein at least a portion of the first time period differs from at least a portion of the second time period; and
   an assignment unit configured to assign a risk score for the suspected heart rhythm disorder based at least in part on the signal changes calculated by the diagnostic unit.

17. The apparatus of claim 16, wherein the signals represent action potentials.

18. The apparatus of claim 16, wherein the signal changes in the signal characteristics comprise a change in a slope of a rate-response associated with the signal changes calculated in response to the variation in at least one of rate and regularity induced in the beating human heart.

19. The apparatus of claim 16, further comprising a detection unit to detect conduction slowing.

20. The apparatus of claim 19, wherein the conduction slowing affects at least one of the signal changes calculated in response to the variation in at least one of rate and regularity induced in the beating human heart.

21. The apparatus of claim 16, further comprising a modification unit configured to modify at least one of tissue structure and function of the beating human heart based at least in part on the signal changes calculated in response to the variation in at least one of rate and regularity induced in the beating human heart.

* * * * *